(12) United States Patent
Schaer et al.

(10) Patent No.: US 10,954,347 B2
(45) Date of Patent: *Mar. 23, 2021

(54) HYDROGELS AND METHOD OF MAKING THE SAME

(71) Applicant: Regeltec, Inc., Baltimore, MD (US)

(72) Inventors: Thomas P. Schaer, Landenberg, PA (US); Peter Wilson, Killingworth, CT (US); Erik Brewer, Conshohocken, NJ (US); Anthony Lowman, Clarksboro, NJ (US); Nigel Gordon Smith, North Walsham (GB)

(73) Assignee: REGELTEC, INC., Baltimore, MD (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/856,705

(22) Filed: Apr. 23, 2020

(65) Prior Publication Data
US 2020/0255601 A1    Aug. 13, 2020

Related U.S. Application Data

(63) Continuation of application No. PCT/US2020/012594, filed on Jan. 7, 2020, which is
(Continued)

(51) Int. Cl.
*C08J 3/075* (2006.01)
*A61L 27/36* (2006.01)
(Continued)

(52) U.S. Cl.
CPC .............. *C08J 3/075* (2013.01); *A61L 27/16* (2013.01); *A61L 27/3658* (2013.01);
(Continued)

(58) Field of Classification Search
CPC .... C08J 3/075; C08J 2371/02; C08J 2329/04; C08J 2339/06; C08J 2471/02;
(Continued)

(56) References Cited

U.S. PATENT DOCUMENTS 7,850,730 B2    12/2010 Vresilovic et al.
8,366,778 B2    2/2013 Kita et al.
(Continued)

FOREIGN PATENT DOCUMENTS

WO    WO 2006/105190    10/2006
WO    WO 2009/079507    6/2009
(Continued)

OTHER PUBLICATIONS

Dang et al, Removal of nucleus pulposus from the intervertebral disc—the use of chymopapain enhances mechanical removal with rongeurs: a laboratory study, 2007, BMC Musculoskeletal Disorders, 8:122, pp. 1-4. (Year: 2007).*
(Continued)

*Primary Examiner* — Trevor Love
(74) *Attorney, Agent, or Firm* — Cooley LLP

(57) ABSTRACT

The present disclosure relates to hydrogels and their use for repairing or supplementing body tissue. The hydrogels are capable of safe injection into patients through fine gauge needles and are suitable for repairing, supplementing, or replacing the nucleus pulposus of an intervertebral disc. Methods of manufacturing and methods of using the hydrogels of the present disclosure to repair or replace tissues are also disclosed.

15 Claims, 15 Drawing Sheets

Related U.S. Application Data a continuation-in-part of application No. 16/673,123, filed on Nov. 4, 2019, now abandoned, which is a continuation of application No. 16/241,510, filed on Jan. 7, 2019, now Pat. No. 10,507,264.

(51) Int. Cl.
   *A61L 27/16* (2006.01)
   *A61L 27/52* (2006.01)
   *A61L 27/26* (2006.01)

(52) U.S. Cl.
   CPC ............ *A61L 27/52* (2013.01); *C08J 2329/04* (2013.01); *C08J 2339/06* (2013.01); *C08J 2371/02* (2013.01)

(58) Field of Classification Search
   CPC ............... C08J 2439/06; C08J 2429/04; A61L 27/3658; A61L 27/16; A61L 27/52; A61L 27/26; A61L 2400/06; A61L 2430/38
   See application file for complete search history.

(56) References Cited

U.S. PATENT DOCUMENTS

| | | | |
|---|---|---|---|
| 8,475,532 B2 | 7/2013 | Vresilovic et al. |
| 8,617,519 B2 | 12/2013 | Binetti et al. |
| 8,703,157 B2 | 4/2014 | Kita et al. |
| 9,078,953 B2 | 7/2015 | Kita et al. |
| 10,507,264 B1 | 12/2019 | Lowman et al. |
| 2006/0122704 A1 | 6/2006 | Vresilovic et al. |
| 2006/0276802 A1 | 12/2006 | Vresilovic et al. |
| 2007/0275030 A1 | 11/2007 | Muratoglu et al. |
| 2010/0272672 A1 | 10/2010 | Kita et al. |
| 2010/0286786 A1 | 11/2010 | Kita et al. |
| 2011/0270400 A1 | 11/2011 | Kita et al. |
| 2011/0276140 A1 | 11/2011 | Vresilovic et al. |
| 2013/0012913 A1 | 1/2013 | Binetti et al. |
| 2018/0168940 A1 | 6/2018 | Hiramatsu et al. |

FOREIGN PATENT DOCUMENTS

| | | |
|---|---|---|
| WO | WO 2009/089526 | 7/2009 |
| WO | WO 2009/146331 | 12/2009 |
| WO | WO 2013/006237 | 1/2013 |
| WO | WO 2017/214635 | 12/2017 |

OTHER PUBLICATIONS

Binetti, Development and Characterization of a Chemically Cross-linked Polyvinyl Alcohol/Polyethylene Glycol Hydrogel for Injectable Nucleus Pulposus Replacement, May 2013, Thesis—Drexel University, 289 pages.

International Search Report and Written Opinion dated Jun. 5, 2020, for International Application No. PCT/US2020/012594, 10 pages.

\* cited by examiner

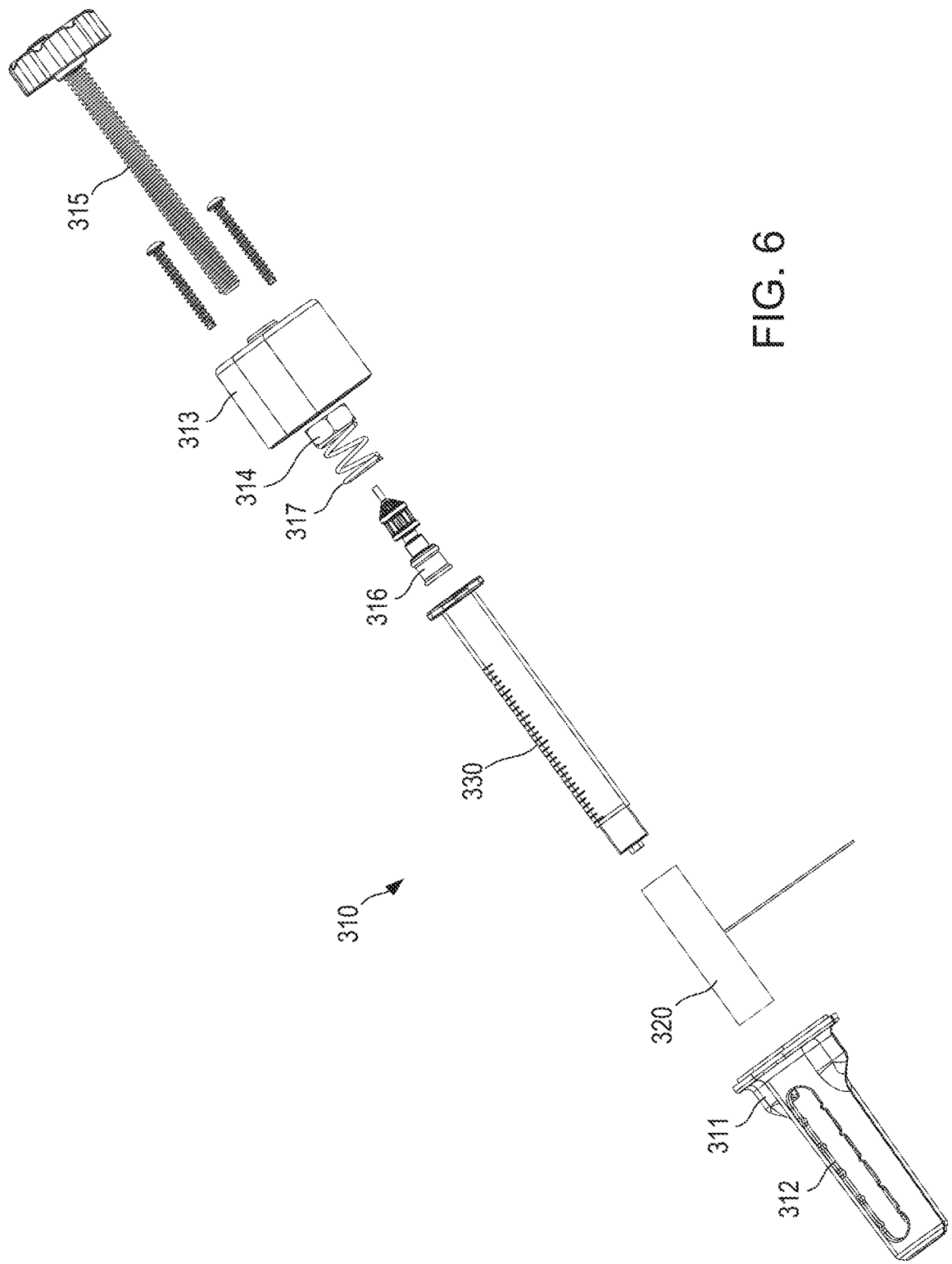

HYDROGELS AND METHOD OF MAKING THE SAME

CROSS-REFERENCE TO RELATED APPLICATIONS

This application is a continuation of International Application No. PCT/US2020/12594, filed Jan. 7, 2020, which is a continuation-in-part of U.S. application Ser. No. 16/673,123, filed Nov. 4, 2019, which is a continuation of U.S. application Ser. No. 16/241,510, filed Jan. 7, 2019, now U.S. Pat. No. 10,507,264, the contents of which are hereby incorporated by reference in their entirety herein.

FIELD OF THE DISCLOSURE

The present disclosure relates to hydrogels and their use for repairing or supplementing body tissue. The hydrogels are capable of safe injection into patients through fine gauge needles using delivery systems described herein and are suitable for repairing or supplementing the nucleus pulposus of an intervertebral disc.

BACKGROUND OF THE INVENTION

According to an extensive 2011 Institute of Medicine Report on chronic pain, approximately 100 million U.S. adults suffer from some form of chronic pain and low back pain is the most common contributor. Lifetime adult incidence of back pain is estimated at 70-80% and it is the second leading cause of physicians' visits. In the United States, back pain is the most common workers compensation claim and in 1999 it was estimated that 149 million workdays are lost every year due to low back pain and the total costs of low back pain are estimated at $50B-$60B per year. In the United Kingdom, where the population is ~$\frac{1}{5}^{th}$ that of the United States, more than 100 million work days are lost every year. The global burden of back pain is estimated in the hundreds of billions of dollars range.

There are a number of causes of back pain but the most prevalent cause is degenerative disc disease. The human intervertebral disc is comprised of two major structures, an outer or peripheral tendinous structure, and an inner gelatinous nucleus pulposus located in a generally central region. Degeneration of the nucleus pulposus, which is typically associated with natural aging, may lead to disc degradation and loss of function.

Many patients experience chronic back pain caused by injury or age-related degeneration of an intervertebral disc. Current treatments range from conservative care to invasive surgical procedures, including discectomy, spinal fusion and total disc replacement. Conservative care often consists of some combination of rest, physical therapy, exercise, weight loss, yoga and pain medicines (such as opioids). Some patients with chronic back pain receive steroids injections and/or injections of pain medicines. Unfortunately, none of the conservative care options addresses the underlying degeneration of the intervertebral disc and there are limited options for patients who fail conservative care other than surgical interventions like discectomy, spinal fusion and total disc replacement. While numerous studies have shown that opioid pain killers are ineffective at alleviating chronic back pain, approximately half of all opioid prescriptions are for chronic back pain. There is a need for a percutaneous treatment option that addresses disc degeneration for patients with chronic back pain who fail conservative care.

Replacement or supplementation of the nucleus pulposus can relieve pain, restore healthy physiologic function to the disc and/or prevent additional wear or deterioration of the annulus. Currently, few minimally invasive techniques or materials exist for supplementation or replacement of the nucleus pulposus of a spinal disc into a selected site of a mammal. Even fewer techniques or materials provide the physiological/mechanical properties to restore the damaged disc to its full capacity.

Existing hydrogel technologies for supplementing or repairing the nucleus pulposus require the injection of solid, often pre-heated, hydrogels through a large gauge needle into the intervertebral space. The resulting punctures may cause severe patient discomfort and provide an opening through which the resulting implant may be expelled. Thus, there is a need for hydrogels that permit injection via fine gauge needles (15 gauge and finer) at temperatures that can be tolerated by a patient (for example, about 65° C. or less at the injection site) while providing tissue implants that possess the required mechanical properties to support an intervertebral disc and do not expulse when a person resumes physical activity.

SUMMARY OF THE INVENTION

In one aspect, the present disclosure provides hydrogels that are suitable for safe injection into the tissue of a living patient in need of repair or supplement through fine gauge needles (e.g., a 15-gauge needle or smaller) to provide tissue implants with mechanical properties that are suitable for the intended use. In some embodiments, the hydrogels are suitable for the repair and/or supplement of the nucleus pulposus of a patient in need thereof.

In some embodiments, the present disclosure provides hydrogels comprising: at least one polymer; and a solvent, wherein at a temperature of about 65° C. the hydrogel is capable of injection through a 16 cm length, 15 gauge needle (or smaller) at an injection rate of at least 1.0 cc per minute using an injection pressure of about 25 psi to provide a tissue implant having a Young's modulus of between about 0.1 to 5.0 MPa.

In some embodiments, the present disclosure provides hydrogels comprising: at least one polymer; and a solvent, wherein at a temperature of about 65° C. the hydrogel is capable of safe injection into the nucleus of an intervertebral disc of a living patient through a 16 cm length, 15 gauge needle (or smaller) to provide a tissue implant having a Young's modulus of between about 0.1 to 5.0 MPa.

In certain embodiments, the at least one polymer is selected from the group consisting of polyvinyl alcohol, polyvinylpyrrolidone, and polyethylene glycol. In some embodiments, the hydrogel polymers comprise a mixture of polyvinyl alcohol, polyvinylpyrrolidone, and polyethylene glycol. In some embodiments, the hydrogel polymers consist essentially of polyvinyl alcohol, polyvinylpyrrolidone, and polyethylene glycol.

In some embodiments, the hydrogels of the present disclosure comprise:
  (a) about 12 wt. % to about 22 wt. % of polyvinyl alcohol;
  (b) about 0.12 wt. % to about 0.22 wt. % of polyvinylpyrrolidone; and
  (c) about 12 wt. % to about 22 wt. % of polyethylene glycol.

In one aspect, the present disclosure provides kits comprising a hydrogel of the present disclosure packaged in a suitable container. In some embodiments, the kits further comprise a hydrogel delivery device. In particular embodiments, the hydrogel delivery device is the device shown in FIG. 1, FIG. 2, and/or FIGS. 3-7B, and/or any suitable combination thereof.

In one aspect, the present disclosure provides methods of making the hydrogels described herein. In some embodiments, the present disclosure provides hydrogels that are prepared according to the methods described herein (i.e., product-by-process).

In one aspect, the present disclosure provides tissue implants having a Young's modulus of between about 0.1 to 5.0 MPa that are prepared by injecting the hydrogels of the present disclosure into the tissue of a patient in need thereof. In some embodiments, the tissue implants of the present disclosure have a Young's modulus of about 0.1 MPa to about 1.0 MPa.

In one aspect, the present disclosure provides methods of using the hydrogels described herein to repair and/or supplement the tissue of a patient in need thereof. In some embodiments, present disclosure provides methods of using the hydrogels to repair, supplement and/or replace the nucleus pulposus of a patient in need thereof.

BRIEF DESCRIPTION OF THE DRAWINGS

The accompanying drawings, which are incorporated herein and constitute part of this specification, illustrate embodiments of the invention, and, together with the general description given above and the detailed description given below, serve to explain the features of the invention. In the drawings:

FIG. 6 is an exploded perspective view of the hydrogel delivery device of FIG. 5.

DEFINITIONS

Figure 1:
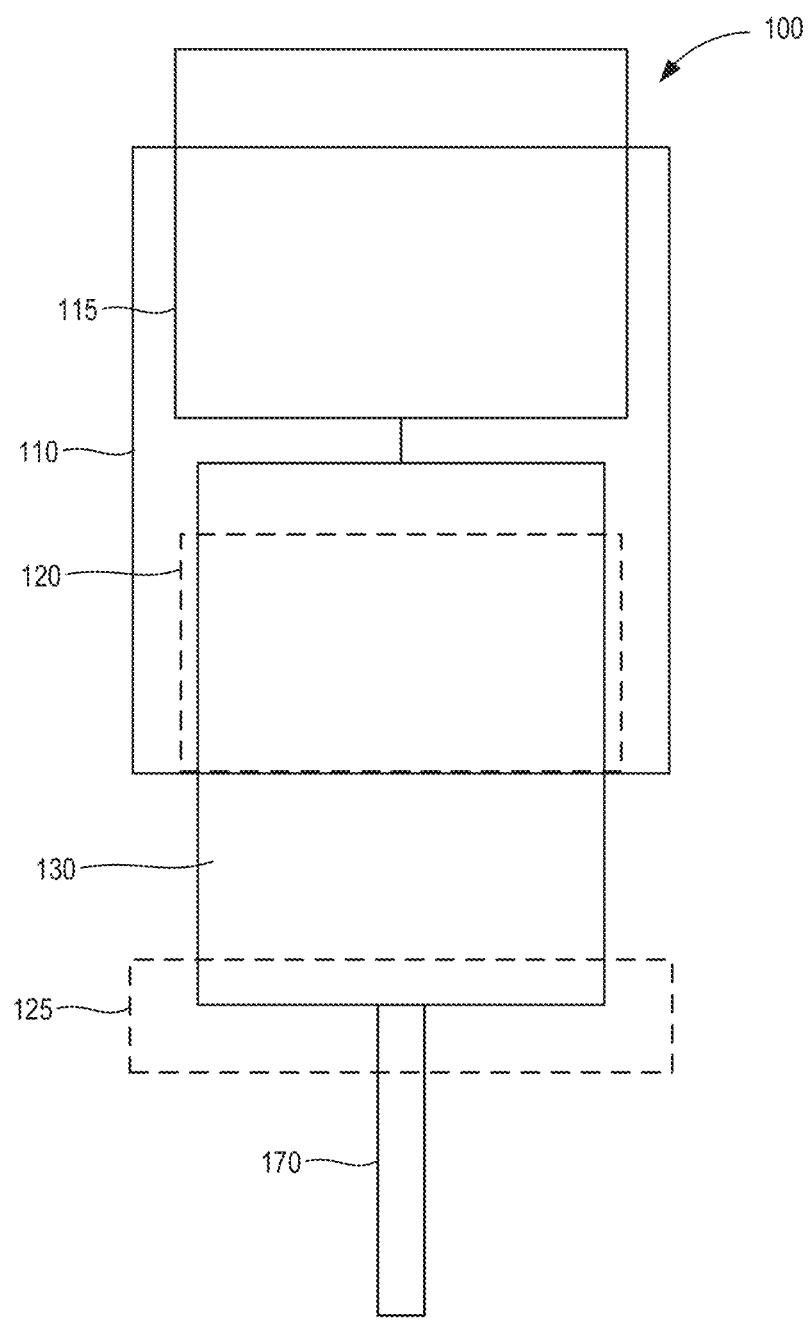
FIG. 1 is a schematic illustration of a hydrogel delivery assembly according to an embodiment.

The term "about" when immediately preceding a numerical value means a range (e.g., plus or minus 10% of that value). For example, "about 50" can mean 45 to 55, "about 25,000" can mean 22,500 to 27,500, etc., unless the context of the disclosure indicates otherwise, or is inconsistent with such an interpretation. For example in a list of numerical values such as "about 49, about 50, about 55, . . . ", "about 50" means a range extending to less than half the interval(s) between the preceding and subsequent values, e.g., more than 49.5 to less than 52.5. Furthermore, the phrases "less than about" a value or "greater than about" a value should be understood in view of the definition of the term "about" provided herein. Similarly, the term "about" when preceding a series of numerical values or a range of values (e.g., "about 10, 20, 30" or "about 10-30") refers, respectively to all values in the series, or the endpoints of the range.

Similarly, the term "substantially" when used in connection with stated value(s) and/or geometric characteristic(s) (e.g., geometric structure(s), geometric relationship(s), and/or the like) is intended to convey that the value or characteristic so defined is nominally the value stated or characteristic described. In some instances, the term "substantially" can generally mean and/or can generally contemplate a value or characteristic stated within a desirable tolerance (e.g., plus or minus 10% of the value or characteristic stated). For example, a first surface may be described as being substantially parallel to a second surface when the surfaces are nominally parallel. While a value, structure, and/or relationship stated may be desirable, it should be understood that some variance may occur as a result of, for example, manufacturing tolerances or other practical considerations (such as, for example, the pressure or force applied through a portion of a device, conduit, lumen, etc.). Accordingly, the term "substantially" can be used herein to account for such tolerances and/or considerations.

Additionally, the term "or" is intended to mean an inclusive "or" rather than an exclusive "or". That is, unless specified otherwise, or clear from context, "X employs A or B" is intended to mean any of the natural inclusive permutations. That is, if X employs A; X employs B; or X employs both A and B, then "X employs A or B" is satisfied under any of the foregoing instances. In addition, the articles "a" and "an" as used in this application and the appended claims should generally be construed to mean "one or more" unless specified otherwise or clear from context to be directed to a singular form.

Throughout this disclosure, various patents, patent applications and publications are referenced. The disclosures of these patents, patent applications and publications in their entireties are incorporated into this disclosure by reference for all purposes in order to more fully describe the state of the art as known to those skilled therein as of the date of this disclosure. This disclosure will govern in the instance that there is any inconsistency between the patents, patent applications and publications cited and this disclosure.

For convenience, certain terms employed in the specification, examples and claims are collected here. Unless defined otherwise, all technical and scientific terms used in this disclosure have the same meanings as commonly understood by one of ordinary skill in the art to which this disclosure belongs.

The terms "effective amount" and "therapeutically effective amount" are used interchangeably in this disclosure and refer to an amount of a hydrogel, that when injected into a patient's tissue, is capable of forming a tissue implant that in turn performs the intended result. For example, an effective amount of the hydrogel of the present disclosure is that amount that is required to improve at least one measurable property (such as radiographic disc height) and/or reduce at least one symptom of a patient who receives the hydrogel injection. The actual amount that comprises the "effective amount" or "therapeutically effective amount" will vary depending on a number of conditions including, but not limited to, the area where the hydrogel is injected, the severity of the disorder, the size and health of the patient. A skilled medical practitioner can readily determine the appropriate amount using methods known in the medical arts.

The words "right", "left", "top" and "bottom" designate directions in the drawings to which reference is made. The words "inwardly" and "outwardly" refer to directions toward and away from, respectively, the geometric center of the device and/or designated parts thereof. The words, "anterior", "posterior", "superior", "inferior", "lateral", and related words and/or phrases designate preferred positions and orientations in the human body to which reference is made and are not meant to be limiting. The words "proximal" and "distal" refer to the direction closer to and away from, respectively, a user who would place a device or the like into contact with a patient (e.g., an end of a device first touching the body of the patient would be the distal end, while the opposite end of the device would be the proximal end of the device). All percentages, unless otherwise indicated, are on a weight-to-weight (wt./wt.) basis. The terminology includes the above-listed words, derivatives thereof and words of similar import.

Any of the embodiments and/or devices used to deliver the hydrogels described herein (and/or portions thereof) can be formed or constructed of one or more biocompatible materials. In some embodiments, the biocompatible materials can be selected based on one or more properties of the constituent material such as, for example, stiffness, toughness, durometer, bioreactivity, etc. Examples of suitable biocompatible materials include but are not necessarily limited to metals, metal alloys, glasses, ceramics, biodegradable polymers, non-biodegradable polymers, and/or combinations thereof. Examples of suitable metals may include pharmaceutical grade stainless steel, gold, titanium, nickel, iron, platinum, tin, chromium, copper, and/or alloys thereof. Examples of suitable biodegradable polymers may include polylactides, polyglycolides, polylactide-co-glycolides, polyanhydrides, polyorthoesters, polyetheresters, polycaprolactones, polyesteramides, poly(butyric acid), poly(valeric acid), polyurethanes, biodegradable polyamides (nylons), and/or blends and copolymers thereof. Examples of non-biodegradable polymers include non-degradable polyamides (nylons), polyesters, polycarbonates, polyacrylates, polymers of ethylene-vinyl acetates and other acyl substituted cellulose acetates, non-degradable polyurethanes, polystyrenes, polyvinyl chloride, polyvinyl fluoride, poly(vinyl imidazole), chlorosulphonate polyolefins, polyethylene oxide, polyetheretherketone (PEEK), and/or blends and copolymers thereof.

DETAILED DESCRIPTION

Certain chemically cross-linked and non-chemically cross-linked hydrogels are suitable for nucleus pulposus replacement and supplementation to repair the intervertebral disc as well as other biomedical applications.

U.S. Pat. Nos. 7,214,245 and 8,703,157 (which are hereby incorporated by reference in their entireties) in combination disclose hydrogels and biomaterials comprising non-chemically cross-linked polymers for repairing the nucleus pulposus and other biomedical applications. The hydrogels described in these references can be applied as solids or, alternatively, as viscous fluids that, when injected into a patient, form tissue implants with mechanical properties that are applicable for the nucleus pulposus and other structural systems. However, as shown in the Examples, the hydrogels described in U.S. Pat. No. 8,703,157 (the '157 patent) are injected at very high temperature (about 95° C.) and use relatively large gauge needles (2.5 mm ID or ~10-11 G) (see Example 11 of the '157 patent).

U.S. Pat. No. 8,617,519 (the '519 patent) discloses chemically cross-linked hydrogels that are said to be flowable when heated above the melting temperature and provide an elastic solid at physiological temperature. However, the '519 patent does not exemplify the injection of the hydrogels through fine gauge needles, and the viscosity measurements that the Applicants rely on to support the injectability of the hydrogels were determined at very high temperature (about 95° C., see Examples 4 and 5 of the '519 patent).

Thus, existing hydrogel technologies are limited in their medical utility since their injection requires very high temperature and/or large gauge needles. For example, injecting hydrogels into patients at high temperatures (above about 65° C. at the injection site) exposes the surgeon (or other trained professional injecting the hydrogel) and the patient to burn risks, which is not commercially viable in the healthcare setting. Furthermore, the use of large gauge needles (as required by existing hydrogel technologies) is particularly problematic in the repair of the nucleus pulposus. First, puncturing the intervertebral disc annulus with a large gauge needle (>15 gauge) increases the risk of damage to the nucleus and can accelerate the disc degeneration process that the hydrogel is intended to treat. Additionally, large-gauge needles create large defect in the annulus during the hydrogel implantation, which increases the likelihood that the implant will be expulsed out of the borehole when the patient resumes normal physical activity. Expulsion is a primary reason previous nucleus augmentation and replacement technologies have failed, since expulsion risk is particularly high with hydrogels that provides implants with "stick"- or "spaghetti" like shape (discussed infra).

Accordingly, there is a need for hydrogels that permit injection via fine gauge needles (15 gauge and finer) while providing tissue implants that possess the required mechanical properties to support an intervertebral disc. Furthermore, there is a need for apparatus, devices, and/or systems configured to inject such hydrogels using fine gauge needles.

The present disclosure provides hydrogels that may be safely injected as viscous solutions through fine gauge needles to form, upon cooling to body temperature, a contiguous hydrogel implant inside the intervertebral disc, which reduces the risk of expulsing the implant and provides suitable mechanical properties for disc repair, supplementation or replacement.

Hydrogels and Kits:

In one aspect, the present disclosure provides hydrogels that are capable of safe injection through a fine gauge needle (smaller than 15 gauge, e.g., 17 or 19 gauge) into a living patient and, upon injection, form tissue implants that are suitable as biomaterials. In particular, at temperatures and pressures that are safe for injection into a living patient (for example, for the repair or supplementation of the nucleus pulposus less than about 65° C. at the injection site and about 60 psi to about 250 psi), the hydrogels of the present disclosure form an injectable composition that when injected into a patient in need thereof solidifies in situ when the implant cools to body temperature to form a suitable hydrogel tissue implant.

The hydrogels of the present disclosure may be safely injected into living patients because, upon heating, the hydrogels undergo a phase transition (i.e., hydrogel melts to provide polymer solution) to provide a polymer solution with a viscosity that allows safe injection into the intervertebral disc space. Furthermore, because the presently-disclosed hydrogels are injectable as polymer solutions, the polymer solution fills the intervertebral disc space and provides a contiguous hydrogel implant (i.e., an implant that fills the disc space into which it is injected) upon cooling to body temperature. Because the hydrogels of the present disclosure fill the intervertebral disc, the resulting implants restores disc height and proper disc biomechanics thereby decreasing pressure on the spinal nerves.

In contrast, previous attempts to develop hydrogels for nucleus augmentation and replacement (such as the hydrogels described in U.S. Pat. No. 7,214,245) provided "spaghetti"-like hydrogel implants when injected because these hydrogels do not undergo a phase transition. Instead, when heated to a relatively high temperature, these hydrogels merely softened so that, using a large-bore needle, the softened hydrogel is injected into the intervertebral disc space that, instead of filling the disc space, forms a spaghetti-like implant that does not properly fit the disc space upon cooling. "Spaghetti"-like implants are susceptible to expulsion and do not mimic the native disc structure. In contrast, the contiguous implants that result from the hydrogels of the present disclosure are less susceptible to expulsion and mimic the native disc structure providing suitable mechanical properties for nucleus repair and replacement.

Figure 14:
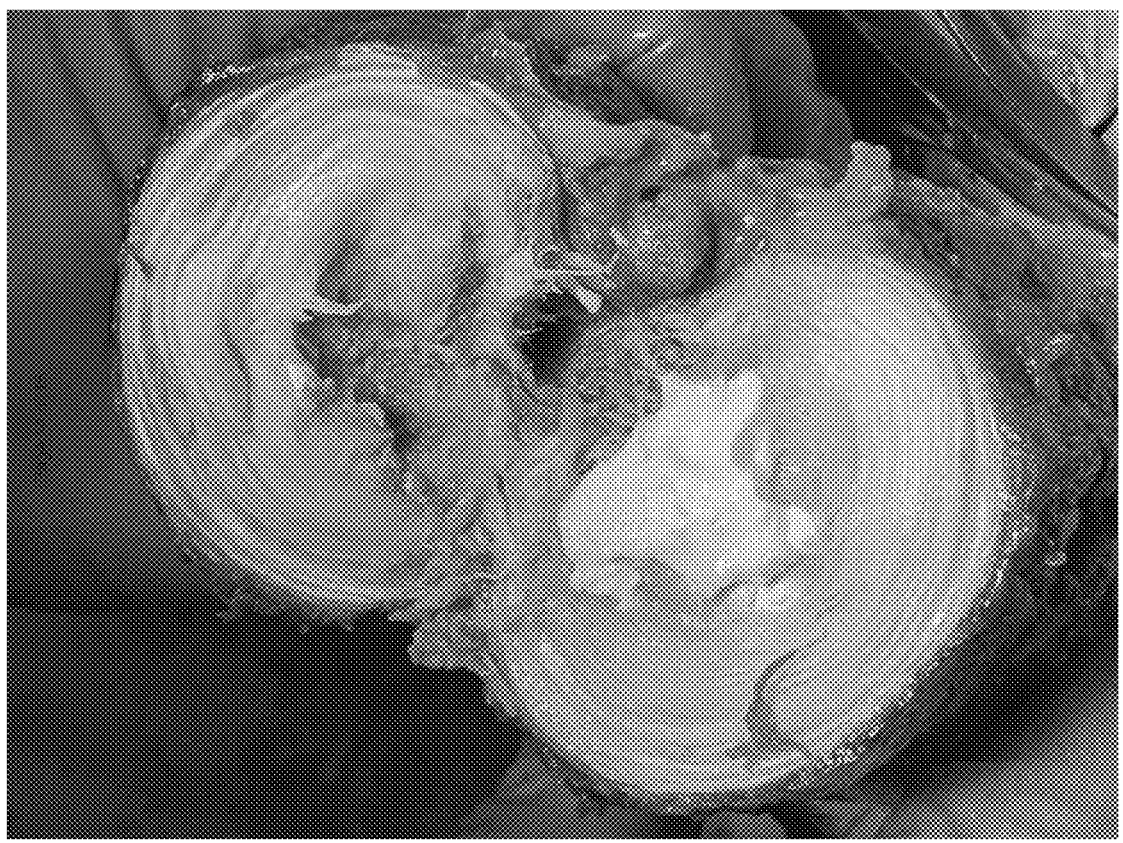
FIG. 14 shows a contiguous nucleus implant that results from injection of a hydrogel of the present disclosure into the intervertebral disc within a human cadaveric lumbar spine.
Figure 15:
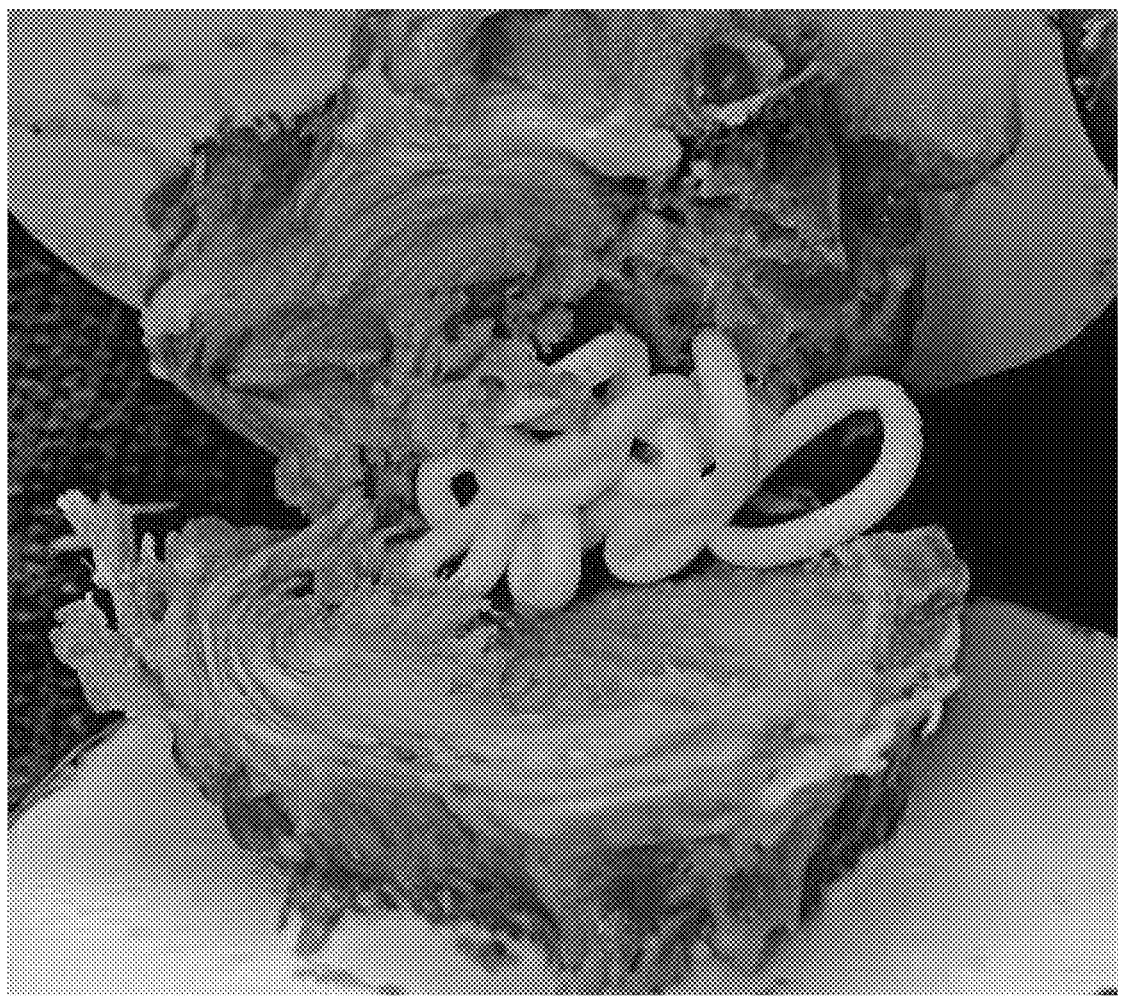
FIG. 15 shows a "spaghetti"-like nucleus implant that results from injection of a hydrogel described in U.S. Pat. No. 7,214,245 the intervertebral disc within a human cadaveric lumbar spine.

FIG. 14 shows a contiguous nucleus implant that results from injection of a hydrogel of the present disclosure (as described in Example 1a) into the intervertebral disc within a human cadaveric lumbar spine. FIG. 15 shows a "spaghetti"-like nucleus implant that results from injection of a hydrogel described in U.S. Pat. No. 7,214,245 into the intervertebral disc within a human cadaver model of the lumbar spine.

The hydrogels of the present disclosure are well suited for repairing a degenerated or damaged intervertebral disc. The hydrogels are useful as a full nucleus pulposus replacement or partial supplementation, as well as for repairing defects, tears or fissures in the disc annulus.

In some embodiments, the hydrogels of the present disclosure are described on the basis of the composition of the polymers in the hydrogel. In some embodiments, the present disclosure provides a hydrogel, where the polymer comprises polyvinyl alcohol, polyethylene glycol and an associating polymer. In some embodiments, the present disclosure provides a hydrogel, where the polymer consists essentially of polyvinyl alcohol, polyethylene glycol and an associating polymer.

In some embodiments, the associating polymer is selected from the group consisting of polyvinylpyrrolidone (PVP), N-(2-hydroxypropyl) methacrylamide (HMPA), xanthan gum, guar gum, pectin, N-carboxymethyl chitosan, polyacrylic acid, hydroxypropyl cellulose (HPC), hydroxypropyl methylcellulose (HPMC), hyaluronic acid, amylose, amylopectin, dextran, and polyacrylamide. In certain embodiments, the associating polymer is polyvinylpyrrolidone.

The hydrogels of the present disclosure may include a suitable solvent. In some embodiments, the suitable solvent is selected from the group consisting of water, saline, phosphate buffer, N-methyl-2-pyrrolidone, dimethylsulfoxide, and an aqueous solution of a $C_1$-$C_6$ alcohol (e.g., methanol, ethanol, ethylene glycol). In certain embodiments, the solvent is water.

In some embodiments, the hydrogel contains a contrast agent. The purpose of the contrast agent is to allow the implant to be imaged using standard methods after injection and to confirm the implant was properly placed and that an adequate volume of hydrogel was used in the injection. Suitable contrast agents are known to those skilled in the art. In some embodiments, the contrast agent is selected from the group consisting of an iodine compound, silver, and a silver salt and a calcium salt (such as hydroxylapatite). In some embodiments, the contrast agent is barium sulfate. In other embodiments, the contrast agent is silver sulfate.

In some embodiments, the present disclosure provides a hydrogel, where the polymer comprises polyvinyl alcohol, polyethylene glycol and PVP. In some embodiments, the present disclosure provides a hydrogel, where the polymer consists essentially of polyvinyl alcohol, polyethylene glycol and PVP.

In some embodiments, the hydrogel comprises
(a) about 12 wt. % to about 22 wt. % of polyvinyl alcohol;
(b) about 0.12 wt. % to about 0.22 wt. % of polyvinylpyrrolidone; and
(c) about 12 wt. % to about 22 wt. % of polyethylene glycol.

In some embodiments, the hydrogel comprises
(a) about 12 wt. % to about 22 wt. % of polyvinyl alcohol;
(b) about 0.12 wt. % to about 0.22 wt. % of polyvinylpyrrolidone;
(c) about 12 wt. % to about 22 wt. % of polyethylene glycol; and
(d) about 9 wt. % to about 19 wt. % of a contrast agent.

In some embodiments, the hydrogel comprises
(a) about 14 wt. % to about 20 wt. % of polyvinyl alcohol;
(b) about 0.14 wt. % to about 0.20 wt. % of polyvinylpyrrolidone; and
(c) about 14 wt. % to about 20 wt. % of polyethylene glycol.

In some embodiments, the hydrogel comprises
(a) about 14 wt. % to about 20 wt. % of polyvinyl alcohol;
(b) about 0.14 wt. % to about 0.20 wt. % of polyvinylpyrrolidone;
(c) about 14 wt. % to about 20 wt. % of polyethylene glycol; and
(d) about 11 wt. % to about 17 wt. % of a contrast agent.

In some embodiments, the hydrogel comprises
(a) about 15 wt. % to about 19 wt. % of polyvinyl alcohol;
(b) about 0.15 wt. % to about 0.19 wt. % of polyvinylpyrrolidone; and
(c) about 15 wt. % to about 19 wt. % of polyethylene glycol.

In some embodiments, the hydrogel comprises
(a) about 15 wt. % to about 19 wt. % of polyvinyl alcohol;
(b) about 0.15 wt. % to about 0.19 wt. % of polyvinylpyrrolidone;
(c) about 15 wt. % to about 19 wt. % of polyethylene glycol; and
(d) about 12 wt. % to about 16 wt. % of a contrast agent.

In some embodiments, the hydrogel comprises
(a) about 16 wt. % to about 18 wt. % of polyvinyl alcohol;
(b) about 0.16 wt. % to about 0.18 wt. % of polyvinylpyrrolidone; and
(c) about 16 wt. % to about 18 wt. % of polyethylene glycol.

In some embodiments, the hydrogel comprises
(a) about 16 wt. % to about 18 wt. % of polyvinyl alcohol;
(b) about 0.16 wt. % to about 0.18 wt. % of polyvinylpyrrolidone;
(c) about 16 wt. % to about 18 wt. % of polyethylene glycol; and
(d) about 13 wt. % to about 15 wt. % of a contrast agent.

In some embodiments, the hydrogel comprises
(a) about 17 wt. % of polyvinyl alcohol;
(b) about 0.17 wt. % polyvinylpyrrolidone; and
(c) about 17 wt. % of polyethylene glycol.

In some embodiments, the hydrogel comprises
(a) about 17 wt. % of polyvinyl alcohol;
(b) about 0.17 wt. % polyvinylpyrrolidone;
(c) about 17 wt. % of polyethylene glycol and
(d) about 14 wt. % of a contrast agent.

In a some embodiments, the hydrogel comprises
(a) polyvinyl alcohol;
(b) at least one associating polymer; and
(c) polyethylene glycol
wherein at a temperature of about 65° C. the hydrogel is capable of injection through a 16 cm length, 17 gauge needle at an injection rate of at least 1.0 cc per minute using an injection pressure of about 25 psi to provide a tissue implant having a Young's modulus of between about 0.1 to 5.0 MPa. In certain further embodiments, the associating polymer is polyvinylpyrrolidone.

In a some embodiments, the hydrogel comprises
(a) polyvinyl alcohol;
(b) at least one associating polymer; and
(c) polyethylene glycol
wherein at a temperature of about 65° C. the hydrogel is capable of safe injection into the nucleus of an intervertebral disc of a living patient through a 16 cm length, 17 gauge needle to provide a tissue implant having a Young's modulus of between about 0.1 to 5.0 MPa. In certain further embodiments, the associating polymer is polyvinylpyrrolidone.

In some embodiments, the hydrogel comprises:
(a) polyvinyl alcohol;
(b) at least one associating polymer;
(c) polyethylene glycol and
(d) a contrast agent,
wherein at a temperature of about 65° C. the hydrogel is capable of injection through a 16 cm length, 17 gauge needle at an injection rate of at least 1.0 cc per minute using an injection pressure of about 25 psi to provide a tissue implant having a Young's modulus of between about 0.1 to 5.0 MPa. In certain further embodiments, the associating polymer is polyvinylpyrrolidone.

In some embodiments, the average molecular weight of the polyethylene glycol is about 100 Da to about 4600 Da, including about 200 Da, about 300 Da, about 400 Da, about 500 Da, about 600 Da, about 700 Da, about 800 Da, about 900 Da, about 1000 Da, about 1100 Da, about 1200 Da, about 1400 Da, about 1600 Da, about 1800 Da, about 2000 Da, about 2200 Da, about 2400 Da, about 2600 Da, about 2800 Da, about 3000 Da, about 3200 Da, about 3400 Da, about 3600 Da, about 3800 Da, about 4000 Da, about 4200 Da, and about 4400 Da, and all ranges there in between. In some preferred embodiments, the average molecular weight of the polyethylene glycol is about 800 Da to about 2000 Da. In some preferred embodiments, the average molecular weight of the polyethylene glycol is about 800 Da to about 1200 Da.

In some embodiments, the average molecular weight of the polyethylene glycol is about 100 Da, about 200 Da, about 300 Da, about 400 Da, about 500 Da, about 600 Da, about 700 Da, about 800 Da, about 900 Da, about 1000 Da, about 1100 Da, about 1200 Da, about 1400 Da, about 1600 Da, about 1800 Da, about 2000 Da, about 2200 Da, about 2400 Da, about 2600 Da, about 2800 Da, about 3000 Da, 3200 Da, about 3400 Da, about 3600 Da, about 3800 Da, about 4000 Da, about 4200 Da, about 4400 Da, or about 4600 Da. In some preferred embodiments, the average molecular weight of the polyethylene glycol is about 1000 Da.

In some embodiments, the average molecular weight of the polyvinyl alcohol is about 60,000 Da to about 190,000 Da, including about 65,000 Da, about 70,000 Da, about 75,000 Da, about 80,000 Da, about 85,000 Da, about 90,000 Da, about 95,000 Da, about 100,000 Da, about 105,000 Da, about 110,000 Da, about 115,000 Da, about 120,000 Da, about 125,000 Da, about 130,000 Da, about 135,000 Da, about 140,000 Da, about 145,000 Da, about 150,000 Da, about 155,000 Da, about 160,000 Da, about 165,000 Da, 165,000 Da, about 170,000 Da, about 175,000 Da, about 180,000 Da, and about 185,000 Da, and all ranges there in between. In certain embodiments, the average molecular weight of the polyvinyl alcohol is about 135,000 Da to about 155,000 Da.

In some embodiments, the hydrogels of the present disclosure are not theta-gels. As used herein, the term "theta-gel" means a gel that uses theta-solvent, for example, polyethylene glycol where the average molecular weight is less than about 600 Da. For example, a hydrogel of the present disclosure that is not a theta-gel is a hydrogel comprising PVA and PEG, wherein the average molecular weight of the polyethylene glycol is greater than about 600 Da.

In some embodiments, the average molecular weight of the polyvinyl alcohol is about 60,000 Da, about 65,000 Da, about 70,000 Da, about 75,000 Da, about 80,000 Da, about 85,000 Da, about 90,000 Da, about 95,000 Da, about 100,000 Da, about 105,000 Da, about 110,000 Da, about 115,000 Da, about 120,000 Da, about 125,000 Da, about 130,000 Da, about 135,000 Da, about 140,000 Da, about 145,000 Da, about 150,000 Da, about 155,000 Da, about 160,000 Da, about 165,000 Da, about 170,000 Da, about 175,000 Da, about 180,000 Da, about 185,000 Da or about 190,000 Da. In certain embodiments, the average molecular weight of the polyvinyl alcohol is about 145,000 Da.

In some embodiments, the average molecular weight of the polyvinylpyrrolidone is about 5,000 Da to about 60,000 Da, including about 10,000 Da, about 15,000 Da, about 20,000 Da, about 25,000 Da, about 30,000 Da, about 35,000 Da, about 40,000 Da, about 45,000 Da, about 50,000 Da, and about 55,000 Da, and all ranges there in between. In certain embodiments, average molecular weight of the polyvinylpyrrolidone is about 35,000 Da to about 45,000 Da.

In some embodiments, the average molecular weight of the polyvinylpyrrolidone is about 5,000 Da, about 10,000 Da, about 15,000 Da, about 20,000 Da, about 20,000 Da, about 25,000 Da, about 30,000 Da, about 35,000 Da, about 40,000 Da, about 45,000 Da, about 50,000 Da, about 55,000 Da, or about 60,000 Da. In certain embodiments, average molecular weight of the polyvinylpyrrolidone is about 40,000 Da.

In some embodiments, the K-value of the polyvinylpyrrolidone is about 26 to about 34, including about 27, about 28, about 29, about 30, about 31, about 32 and about 33, and all ranges there in between. In certain embodiments, the K-value of the polyvinylpyrrolidone is about 28 to about 32. The K-values described herein are determined using capillary viscometry according to the method set forth in ISO 1628-1.

In some embodiments, the K-value of the polyvinylpyrrolidone is about 26, about 27, about 28, about 29, about 30, about 31, about 32, about 33 or about 34. In certain embodiments, the K-value of the polyvinylpyrrolidone is about 30.

In some embodiments, the present disclosure provides a hydrogel, comprising:
  about 12 wt. % to about 22 wt. % of polyvinyl alcohol;
  about 0.12 wt. percent to about 0.22 wt. % of polyvinylpyrrolidone;
  about 12 wt. % to about 22 wt. % non-functionalized polyethylene glycol having a Mw of about 800 Da to about 2,000 Da, wherein the hydrogel does not contain a chemically crosslinked polymer.

In some embodiments, the present disclosure provides a hydrogel wherein at a temperature from about 45° C. to about 65° C. the hydrogel is capable of injection through a 16 cm length, 17 gauge needle at an injection rate of at least 0.5 cc per minute using an injection pressure of less than about 200 psi.

In some embodiments, the non-functionalized polyethylene glycol has an Mw of about 800 Da to about 1,200 Da. In some embodiments, the non-functionalized polyethylene glycol has a Mw of about 900 Da to about 1,100 Da. In some embodiments, the non-functionalized polyethylene glycol has a Mw of about 1,000 Da.

In some embodiments, the hydrogels of the present disclosure further comprise a contrast agent. In some embodiments, the contrast agent is barium sulfate.

In some embodiments, the hydrogels of the present disclosure comprise about 9 wt. % to about 19 wt. % of the contrast agent.

In some embodiments, the hydrogels of the present disclosure comprise:
  the polyvinyl alcohol has an Mw of about 135,000 Da to about 155,000 Da;
  the non-functionalized polyethylene glycol has an Mw of about 800 Da to about 1,200 Da; and
  the polyvinylpyrrolidone has an Mw of about 35,000 Da to about 45,000 Da.

In some embodiments, the hydrogels of the present disclosure are characterized on the basis of their unique functional properties. The hydrogels of the present disclosure are capable of injection through fine gauge needles into a living patient's tissue under temperature and pressure conditions that are safe for use in surgical and interventional procedures. As used herein, the phrase "capable of safe injection into a living patient's tissue" is used to functionally describe some embodiments of the hydrogels of the present disclosure and means that the hydrogel may be injected into a patient in need thereof under temperature and pressure conditions that do not cause substantial damage to the tissue surrounding the injection site. The safe injection pressure and temperature will depend in part on the tissue that the hydrogel is injected into and may be determined by those of skill in the art.

As described herein, the pressure during an injection of a hydrogel of the present disclosure is described by the injection pressure or the backpressure. As used herein "injection pressure" is the pressure on the syringe plunger that is sufficient to transfer the hydrogel of the present disclosure through a particular delivery system (e.g., a 17-gauge needle of defined length) at a particular injection rate (e.g., 1.0 cc per minute) and is determined by delivering the hydrogel through the open system (i.e., the hydrogel is passed from the syringe, through the delivery system and into an open space). As used herein "backpressure" is the pressure measured as a hydrogel of the present disclosure is delivered through a particular delivery system (e.g., a 17-gauge needle of defined length) at a particular injection rate (e.g., 1.0 cc per minute) into a closed system (e.g., the intervertebral space). Backpressure increases during the injection as the hydrogel fills the space into which it is injected.

Methods of measuring injection pressure and backpressure are known to those skilled in the art. In some embodiments of the present disclosure, injection pressure is measured by placing a pressure gauge on the plunger of the hydrogel-containing syringe during the injection to record the injection pressure. In some embodiments of the present disclosure, backpressure is measured by placing a 3-way connector between the hydrogel-containing syringe, the cavity into which the hydrogel is injected (e.g., the intervertebral space) and a pressure gauge to record the backpressure.

In some embodiments, the present disclosure provides a hydrogel, comprising: at least one polymer; and a solvent, wherein at a temperature of about 65° C. the hydrogel is capable of injection through a 16 cm length, 17 gauge needle at an injection rate of at least 1.0 cc per minute using an injection pressure of about 25 psi to provide a tissue implant having a Young's modulus of between about 0.1 to 5.0 MPa. In certain embodiments, the at least one polymer is a mixture of polyvinyl alcohol (PVA), polyvinylpyrrolidone (PVP), and polyethylene glycol (PEG). In some embodiments, the hydrogel does not contain a chemically cross-linked polymer.

In some embodiments, the present disclosure provides a hydrogel that is capable of safe injection into the nucleus of an intervertebral disc under injection conditions (e.g., backpressure and temperature) that do not result in endplate damage or promote a herniation through weakness in the annulus fibrosus. In some embodiments, the hydrogel is capable of injection into the nucleus of an intervertebral disc into a living patient through a 16 cm length, 17 gauge needle at a rate of at least 1.0 cc per minute to provide a tissue implant having a Young's modulus of between about 0.1 to 5.0 MPa, wherein the backpressure during the injection is from about 35 psi to about 400 psi, including about 40 psi, about 50 psi, about 60 psi, about 70 psi, about 80 psi, about 90 psi, about 100 psi, about 110 psi, about 120 psi, about 130 psi, about 140 psi, about 150 psi, about 160 psi, about 170 psi, about 180 psi, about 190 psi, about 200 psi, about 210 psi, about 220 psi, about 230 psi, about 240 psi, about 250 psi, about 260 psi, about 270 psi, about 280 psi, about 290 psi, about 300 psi, about 310 psi, about 320 psi, about 330 psi, about 340 psi, about 350 psi, about 360 psi, about 370 psi, about 380 psi, and about 390 psi, and all ranges there in between. In certain embodiments, hydrogel is capable of injection into the nucleus of an intervertebral disc into a living patient through a 16 cm length, 17 gauge needle at a rate of at least 1.0 cc per minute to provide a tissue implant having a Young's modulus of between about 0.1 to 5.0 MPa, wherein the backpressure during the injection is from about 60 psi to about 200 psi.

In some embodiments, the hydrogel is capable of injection into the nucleus of an intervertebral disc into a living patient through a 16 cm length, 17 gauge needle at a rate of at least 1.0 cc per minute to provide a tissue implant having a Young's modulus of between about 0.1 to 5.0 MPa, wherein the maximum backpressure during the injection is less than about 60 psi, about 70 psi, about 80 psi, about 90 psi, about 100 psi, about 110 psi, about 120 psi, about 130 psi, about 140 psi, about 150 psi, about 160 psi, about 170 psi, about 180 psi, about 190 psi, about 200 psi, about 210 psi, about 220 psi, about 230 psi, about 240 psi, about 250 psi, about 260 psi, about 270 psi, about 280 psi, about 290 psi, about 300 psi, about 310 psi, about 320 psi, about 330 psi, about 340 psi, about 350 psi, about 360 psi, about 370 psi, about 380 psi, about 390 psi, and about 400 psi. In certain embodiments, hydrogel is capable of injection into the nucleus of an intervertebral disc into a living patient through a 16 cm length, 17 gauge needle at a rate of at least 1.0 cc per minute to provide a tissue implant having a Young's modulus of between about 0.1 to 5.0 MPa, wherein the maximum backpressure during the injection is less than about 250 psi. In certain embodiments, hydrogel is capable of injection into the nucleus of an intervertebral disc into a living patient through a 16 cm length, 17 gauge needle at a rate of at least 1.0 cc per minute to provide a tissue implant having a Young's modulus of between about 0.1 to 5.0 MPa, wherein the maximum backpressure during the injection is less than about 200 psi.

In some embodiments, the hydrogels of the present disclosure are described on the basis of the needle gauge that the hydrogel at a temperature of about 65° C. is capable of injection through using a 16-cm length needle. In some embodiments, the needle gauge is about 15 gauge to about 22 gauge, including about 16 gauge, about 17 gauge, about 18 gauge, about 19 gauge, about 20 gauge, and about 21 gauge and all ranges there in between. In certain embodiments, the needle gauge is about 17 gauge to about 19 gauge. In some embodiments, the needle gauge is about 15 gauge, about 16 gauge, about 17 gauge, about 18 gauge, about 19 gauge, about 20 gauge, about 21 gauge, and about 22 gauge. In certain embodiments, the needle gauge is about 18 gauge. In certain embodiments, the needle gauge is about 17 gauge. In certain embodiments, the needle is a 152 mm Tuohy epidural needle.

In some embodiments, the hydrogels of the present disclosure are described on the basis of their viscosity at a temperature of about 65° C. In some embodiments, the viscosity of the hydrogel at a temperature of about 65° C. is about 5 Pascal seconds (Pa·s) to about 70 Pa·s, including about 10 Pa·s, about 15 Pa·s, about 20 Pa·s, about 25 Pa·s, about 30 Pa·s, about 35 Pa·s, about 40 Pa·s, about 45 Pa·s, about 50 Pa·s, about 55 Pa·s, about 60 Pa·s, and about 65 Pa·s, and all ranges there in between. In certain embodiments, the viscosity of the hydrogel at a temperature of about 65° C. is about 10 Pa·s to about 60 Pa·s. In some embodiments, the viscosity of the hydrogel at a temperature of about 65° C. is about 5 Pa·s, about 10 Pa·s, about 15 Pa·s, about 20 Pa·s, about 25 Pa·s, about 30 Pa·s, about 35 Pa·s, about 40 Pa·s, about 45 Pa·s, about 50 Pa·s, about 55 Pa·s, about 60 Pa·s, about 65 Pa·s, or about 70 Pa·s. In some embodiments, the viscosity of the hydrogel at a temperature of about 65° C. is about 10 Pa·s. In some embodiments, the viscosity of the hydrogel at a temperature of about 65° C. is 8±2 Pa·s.

In some embodiments, the hydrogels of the present disclosure are described on the basis of their Young's modulus. In some embodiments, the Young's modulus of the hydrogel is about 0.25 MPa. In some embodiments, the Young's modulus of the hydrogel is 0.2±0.05 MPa.

In some embodiments, the hydrogels of the present disclosure are described on the basis of their swelling ratio determined according to the to the 7-day swelling test method in ASTM F2789-10. In some embodiments, the $V/V_0$ of the hydrogel is about 1.0 to about 1.2 determined according to the 7-day swelling test method in ASTM F2789-10.

In some embodiments, the hydrogels of the present disclosure are described on the basis of the injection rate at which they may be injected through a 16 cm length, 17 gauge needle when the temperature of the composition is about 65° C. In some embodiments, the injection rate of the hydrogel is greater than about 1.0 cc/min. In some embodiments, the injection rate of the hydrogel is greater than about 1.5 cc/min. In some embodiments, the injection rate of the hydrogel is greater than about 2.0 cc/min. In some embodiments, the injection rate of the hydrogel is greater than about 2.5 cc/min. In some embodiments, the injection rate of the hydrogel is greater than about 3.0 cc/min. In some embodiments, the injection rate of the hydrogel is greater than about 3.5 cc/min. In some embodiments, the injection rate of the hydrogel is greater than about 4.0 cc/min. In some embodiments, the injection rate of the hydrogel is greater than about 4.5 cc/min. In some embodiments, the injection rate of the hydrogel is greater than about 5.0 cc/min. In some embodiments, the injection rate of the hydrogel is greater than about 5.5 cc/min. In some embodiments, the injection rate of the hydrogel is greater than about 6.0 cc/min.

In some embodiments, the hydrogels of the present disclosure are described on the basis of the injection temperature at which the composition may be injected through a 16 cm length, 17 gauge needle. In some embodiments, the injection temperature is about 40° C. to about 90° C., including about 50° C., about 55° C., about 60° C., about 65° C., about 70° C., about 75° C., about 80° C., and about 85° C., and all ranges there in between. In certain embodiments, the injection temperature is about 45° C. to about 90° C. In certain embodiments, the injection temperature is about 65° C. to about 80° C. In certain embodiments, the injection temperature is about 55° C. to about 70° C. In some embodiments, the injection temperature is about 45° C., about 50° C., about 55° C., about 60° C., about 65° C., about 70° C., about 75° C., about 80° C., about 85° C. or about 90° C. In certain embodiments, the injection temperature is about 80° C. In certain embodiments, the injection temperature is about 65° C.

In some embodiments, the hydrogels of the present disclosure are characterized on the basis of their set up time at body temperature (i.e., the time required for the hydrogel to provide a stable implant after injection into a patient in need thereof). In some embodiments, the set up time of the hydrogels of the disclosure is characterized by providing an implant that does not come back out from puncture resulting from the injection of the hydrogel. In some embodiments, the set up time of the hydrogels of the present disclosure is less than about 20 minutes, less than about 15 minutes or less than about 10 minutes. In some embodiments, the set up time of the hydrogels of the present disclosure is about 20 minutes, about 15 minutes or about 10 minutes.

In one aspect, the present disclosure provides kits containing the compositions of the present disclosure packaged in a suitable container. The volume of the compositions of the present disclosure in the suitable container will depend on the particular application.

In some embodiments, the present disclosure provides a kit for disc augmentation (i.e., repair of a damaged disc). In some embodiments, the present disclosure provides a kit for disc augmentation comprising about 0.1 cc to about 12.0 cc, including about 0.1 cc, about 0.5 cc, about 1.0 cc, about 1.5 cc, about 2.0 cc, about 2.5 cc, about 3.0 cc, about 3.5 cc, about 4.0 cc, about 4.5 cc, about 5.0 cc, about 5.5 cc, about 6.0 cc, about 6.5 cc, about 7.0 cc, about 7.5 cc, about 8.0 cc, about 8.5 cc, about 9.0 cc, about 9.5 cc, about 10.0 cc, about 10.5 cc, about 11.0 cc, about 11.5 cc and about 12.0 cc and all ranges there between, of a composition of the present disclosure packaged in a suitable container. In some embodiments, the present disclosure provides a kit for disc augmentation comprising about 3.0 cc to about 6.0 cc, including about 3.0 cc, about 3.5 cc, about 4.0 cc, about 4.5 cc, about 5.0 cc, about 5.5 cc, and about 6.0 cc, and all ranges there between, of a composition of the present disclosure packaged in a suitable container. In some embodiments, the present disclosure provides a kit for disc augmentation comprising about 4.0 cc to about 6.0 cc, including about 4.0 cc, about 4.5 cc, about 5.0 cc, about 5.5 cc, and about 6.0 cc, and all ranges there between, of a composition of the present disclosure packaged in a suitable container. In some embodiments, the present disclosure provides a kit for disc augmentation comprising about 8.0 cc to about 10.0 cc, including about 8.0 cc, about 8.5 cc, about 9.0 cc, about 9.5 cc, and about 10.0 cc, and all ranges there between, of a composition of the present disclosure packaged in a suitable container. In some embodiments, the present disclosure provides a kit for disc augmentation comprising about 0.5 cc, about 1.0 cc, about 1.5 cc, about 2.0 cc, about 2.5 cc, about 3.0 cc, about 3.5 cc, about 4.0 cc, about 4.5 cc, about 5.0 cc, about 5.5 cc, about 6.0 cc, about 6.5 cc, about 7.0 cc, about 7.5 cc, about 8.0 cc, about 8.5 cc, about 9.0 cc, about 9.5 cc, about 10.0 cc, about 10.5 cc, about 11.0 cc, about 11.5 cc or about 12.0 cc of a composition of the present disclosure packaged in a suitable container. In some embodiments, the present disclosure provides a kit for disc augmentation comprising about 3.0 cc of a composition of the present disclosure packaged in a suitable container. In some embodiments, the present disclosure provides a kit for disc augmentation comprising about 6.0 cc of a composition of the present disclosure packaged in a suitable container. In some embodiments, the present disclosure provides a kit for disc augmentation comprising about 8.0 cc of a composition of the present disclosure packaged in a suitable container.

In some embodiments, the present disclosure provides a kit for nucleus pulposus replacement (i.e., to replace a nucleus pulposus that has been denucleated). In some embodiments, the present disclosure provides a kit for nucleus pulposus replacement comprising about 0.5 cc to about 12.0 cc, including about 0.5 cc, about 1.0 cc, about 1.5 cc, about 2.0 cc, about 2.5 cc, about 3.0 cc, about 3.5 cc, about 4.0 cc, about 4.5 cc, about 5.0 cc, about 5.5 cc, about 6.0 cc, about 6.5 cc, about 7.0 cc, about 7.5 cc, about 8.0 cc, about 8.5 cc, about 9.0 cc, about 9.5 cc, about 10.0 cc, about 10.5 cc, about 11.0 cc, about 11.5 cc and about 12.0 cc and all ranges there between, of a composition of the present disclosure packaged in a suitable container. In some embodiments, the present disclosure provides a kit for nucleus pulposus replacement comprising about 3.0 cc to about 6.0 cc, including about 3.0 cc, about 3.5 cc, about 4.0 cc, about 4.5 cc, about 5.0 cc, about 5.5 cc, and about 6.0 cc, and all ranges there between, of a composition of the present disclosure packaged in a suitable container. In some embodiments, the present disclosure provides a kit for nucleus pulposus replacement comprising about 4.0 cc to about 6.0 cc, including about 4.0 cc, about 4.5 cc, about 5.0 cc, about 5.5 cc, and about 6.0 cc, and all ranges there between, of a composition of the present disclosure packaged in a suitable container. In some embodiments, the present disclosure provides a kit for nucleus pulposus replacement comprising about 8.0 cc to about 10.0 cc, including about 8.0 cc, about 8.5 cc, about 9.0 cc, about 9.5 cc, and about 10.0 cc, and all ranges there between, of a composition of the present disclosure packaged in a suitable container. In some embodiments, the present disclosure provides a kit for nucleus pulposus replacement comprising about 0.5 cc, about 1.0 cc, about 1.5 cc, about 2.0 cc, about 2.5 cc, about 3.0 cc, about 3.5 cc, about 4.0 cc, about 4.5 cc, about 5.0 cc, about 5.5 cc, about 6.0 cc, about 6.5 cc, about 7.0 cc, about 7.5 cc, about 8.0 cc, about 8.5 cc, about 9.0 cc, about 9.5 cc, about 10.0 cc, about 10.5 cc, about 11.0 cc, about 11.5 cc or about 12.0 cc of a composition of the present disclosure packaged in a suitable container. In some embodiments, the present disclosure provides a kit for nucleus pulposus replacement comprising about 3.0 cc of a composition of the present disclosure packaged in a suitable container. In some embodiments, the present disclosure provides a kit for nucleus pulposus replacement comprising about 6.0 cc of a composition of the present disclosure packaged in a suitable container. In some embodiments, the present disclosure provides a kit for nucleus pulposus replacement comprising about 8.0 cc of a composition of the present disclosure packaged in a suitable container.

Suitable containers for packaging the hydrogels of the present disclosure are known to those skilled in the art. In some embodiments, the suitable container is selected from a vial or a syringe. The hydrogels of the present disclosure may be packaged in containers constructed of any suitable material known to those skilled in the art. In some embodiments, the suitable container is glass. In other embodiments, the suitable container is polycarbonate. In certain embodiments, the suitable container is a polycarbonate syringe. In certain embodiments, the suitable container is a glass syringe.

In some embodiments, the kits of the present disclosure further comprise a hydrogel delivery system. Suitable hydrogel delivery systems are capable of receiving a hydrogel of the present disclosure, maintaining the temperature of the hydrogel within a desired range prior to and during injection, and injecting a hydrogel of the present disclosure through a fine gauge needle into the tissue of a patient in need thereof (for example, the nucleus of an intervertebral disc) under temperature and pressure conditions that are safe for injection into a living patient.

In certain embodiments, a hydrogel delivery system or assembly comprises a syringe assembly and any number of other features, components, and/or assemblies configured to facilitate the injection of the hydrogel. For example, FIG. 1 is a schematic illustration of hydrogel delivery assembly 100 according to an embodiment. The hydrogel delivery assembly 100 ("assembly 100") includes at least an injector 110, a syringe 130, and a needle 170. In some embodiments, the assembly 100 optionally includes a heater assembly 120 and a pressure gauge assembly 125. In some implementations, the assembly 100 can be used to inject any of the hydrogels described herein into a nucleus pulposus of a vertebral disc to provide for augmentation, repair, and/or replacement thereof.

The injector 110 can be any suitable shape, size, and/or configuration. As shown in FIG. 1, the injector 110 can be configured to receive, house, and/or contain at least a portion of the syringe 130. In embodiments including a heater assembly 120, the injector 110 can also receive, house, and/or container at least a portion of the heater assembly 120. In some embodiments, for example, the injector 110 can be and/or can form a housing configured to receive and/or house at least a portion of the syringe 130, heater assembly 120, and/or the like. In some embodiments, the injector 110 can define one or more openings, features, windows, etc. configured to allow for visualization of at least some of the components contained and/or housed within the injector 110.

Although not shown in FIG. 1, in some embodiments, the injector 110 can include a bias member and/or mechanism that can selectively engage a portion of the syringe 130 to maintain the syringe 130 in a desired position relative to the injector 110. For example, in some embodiments, the syringe 130 can be maintained in a distal position (e.g., closer to the needle 170) within and/or relative to the injector 110.

The injector 110 includes an actuator 115 configured to actuate and/or manipulate a portion of the syringe 130 disposed within the injector 110. The actuator 115 can be any suitable member, device, assembly, mechanism, etc. configured to actuate and/or manipulate the portion of the syringe 130 (e.g., either directly or indirectly). For example, in some embodiments, the actuator 115 can be and/or can include a plunger, a push rod, a rotationally actuated rod, a lever, a trigger and/or ratchet mechanism, a pumping mechanism, and/or any other suitable actuator. In some implementations, the actuator 115 can be moved, transitioned, actuated, etc. via a manually applied force (e.g., a force exerted by a user), an electric or electronic activation, a chemical activation, and/or any other automatic or manual actuation.

In some implementations, the actuator 115 can be configured to actuate and/or manipulate a seal, plunger, stopper, etc. disposed within the syringe 130 to expel at least a portion of a volume of hydrogel disposed in the syringe 130. For example, in some embodiments, a user can exert a force on a portion of the actuator 115 that can transition the actuator 115 from a first configuration toward a second configuration operable to move the seal or plunger of the syringe 130 to expel at least a portion of the volume of hydrogel disposed therein.

The syringe 130 included in the assembly 100 can be any suitable syringe 130 or any other suitable reservoir. In some embodiments, the syringe 130 can be sized and/or configured to at least temporarily contain a volume of a hydrogel composition between about 0.1 cc to about 12.0 cc, as described above. The syringe 130 can be formed from any suitable material such as, for example, any of the biocompatible materials described above. In some embodiments, the syringe 130 can be formed of a material that is configured to withstand, tolerate, and/or otherwise be compatible with temperatures sufficient to maintain the hydrogel composition in a substantially viscous state (e.g., between about 40° C. and about 90° C.). In some embodiments, the syringe 130 can be formed of a material that is compatible with temperatures associated with an initial heating of the hydrogel prior to being conveyed into the syringe 130 (e.g., about 121° C. or more). In some embodiments, the syringe 130 can be formed from a material with a thermal conductivity that can allow the syringe 130 to transfer thermal energy received (e.g., directly or indirectly) from the optional heater assembly 120 to the hydrogel contained within the syringe 130.

The needle 170 is coupled to a discharge (e.g., distal) end portion of the syringe 130. In some embodiments, a proximal end portion of the needle 170 is directly coupled to the discharge end via any suitable coupling such as, for example, a luer connection. In other embodiments, the proximal end portion of the needle 170 is indirectly coupled to the discharge end portion via any suitable intermediate device such as, for example, flexible tubing, and/or the like. The needle 170 has a distal or discharge end that is configured for insertion through the wall of an intervertebral disc and into the nucleus pulposus for injection of the hydrogel. In some embodiments, the needle 170 can be between a 15 gauge needle and a 22 gauge needle. In other embodiments, the gauge of the needle 170 is greater than 15 gauge (e.g., 12 gauge, 11 gauge, 10 gauge, etc.) or less than 22 gauge (e.g., 24 gauge, 26 gauge, 27 gauge, etc.). In some instances, the use of a fine gauge needle 170 (e.g., 15 gauge or smaller) can reduce and/or can substantially minimize the size of the injection opening through the wall of the disc, thereby reducing and/or substantially minimizing the size of the opening through which the hydrogel can escape from the disc after the needle 170 is removed following injection (e.g., relative to the use of larger-gauge needles).

As described above, the assembly 100 can optionally include the heater assembly 120 and the pressure gauge assembly 125. The heater assembly 120 can be any suitable heating device or the like. For example, in some embodiments, the heater assembly 120 can be and/or can include an electric heater (e.g., configured to receive AC electric power or DC electric power). In some embodiments, the heater assembly 120 can be configured to at least partially wrap around and/or otherwise at least partially surround a portion of the syringe 130. In some embodiments, for example, the heater assembly 120 can be a sleeve or the like in or through which the syringe 130 can be inserted. In some embodiments, the heater assembly 120 can be in contact with a surface of the syringe 130 to allow for direct thermal contact and/or transfer therebetween. In other embodiments, the heater assembly 120 can be positioned within the injector 110 adjacent to but not in contact with the syringe 130, resulting in indirect thermal contact and/or transfer therebetween. In still other embodiments, the heater assembly 120 can be at least partially integrated into the syringe 130 (e.g., a heating coil or wire embedded in a body and/or plunger of the syringe 130).

The pressure gauge assembly 125 can be any suitable pressure gauge, monitor, regulator, and/or the like. In some embodiments, the pressure gauge assembly 125 can be coupled between the distal or discharge end portion of the syringe 130 and the proximal end portion of the needle 170. In other embodiments, the pressure gauge assembly 125 can be coupled to and/or integral with the distal end portion of the syringe 130 or the proximal end portion of the needle 170. In still other embodiments, the pressure gauge assembly 125 can be coupled to and/or can include an intermediate device or tubing positioned between the distal end portion of the syringe 130 and the proximal end portion of the needle 170. In some implementations, the pressure gauge assembly 125 can be configured to determine, monitor, test, regulate, and/or indicate a backpressure associated with and/or resulting from injection of the hydrogel into the nucleus pulposus of the disc. In some implementations, a suitable backpressure can be between about 35 psi and about 300 psi, between about 60 psi and about 250 psi, about 200 psi, and/or any other suitable backpressure, as described above.

In other embodiments, the pressure gauge assembly 125 can be coupled to and/or integrated with a portion of the actuator 115 and/or the plunger of the syringe 130. In some implementations, such a pressure gauge assembly 125 can be configured to determine, monitor, test, regulate, and/or indicate an injection pressure associated with expelling and/or injecting the hydrogel. In some implementations, a suitable injection pressure can be between about 25 psi and about 250 psi, as described above.

The assembly 100 can be used to inject any of the hydrogels described herein into a nucleus pulposus of a vertebral disc to provide for augmentation, repair, and/or replacement thereof. For example, a method of using the assembly 100 can include melting a hydrogel of the present disclosure (e.g., in some embodiments, heating to about 121° C. in an autoclave) and conveyed into the syringe 130. The syringe 130 can be positioned within the injector 110 prior to or after receiving the hydrogel. In some embodiments, a bias mechanism or the like included in the injector 110 can bias the syringe 130 in a predetermined and/or desired position (e.g., a distal position) within and/or relative to the injector 110. In some embodiments, optional heating assembly 120 can be configured to transfer thermal energy to or through the syringe 130 to optionally melt the hydrogel (e.g., between about 90° C. and about 121° C.) and maintain the hydrogel at a desired injection temperature (e.g., between about 40° C. and about 90° C., as described above). A user such as, a surgeon, doctor, interventional radiologist, technician, etc., can manipulate the assembly 100 to insert the distal end portion of the needle 170 through bodily tissue of the patient, through a wall of a vertebral disc, and into the nucleus pulposus of the disc. Once inserted, the actuator 115 can be actuated to inject at least a portion of the hydrogel contained in the syringe 130 into the disc. In some implementations, the optional pressure gauge assembly 125 can be used to monitor an injection pressure and/or a backpressure associated with expelling and/or injecting the hydrogel. A desired volume of hydrogel (e.g., between about 0.1 cc and about 12.0 cc) can be injected with any suitable injection pressure, backpressure, and/or flow rate, such as any of those described above. After conveying a therapeutically effective volume of hydrogel to the disc, the needle 170 can be removed from the patient.

Figure 2:
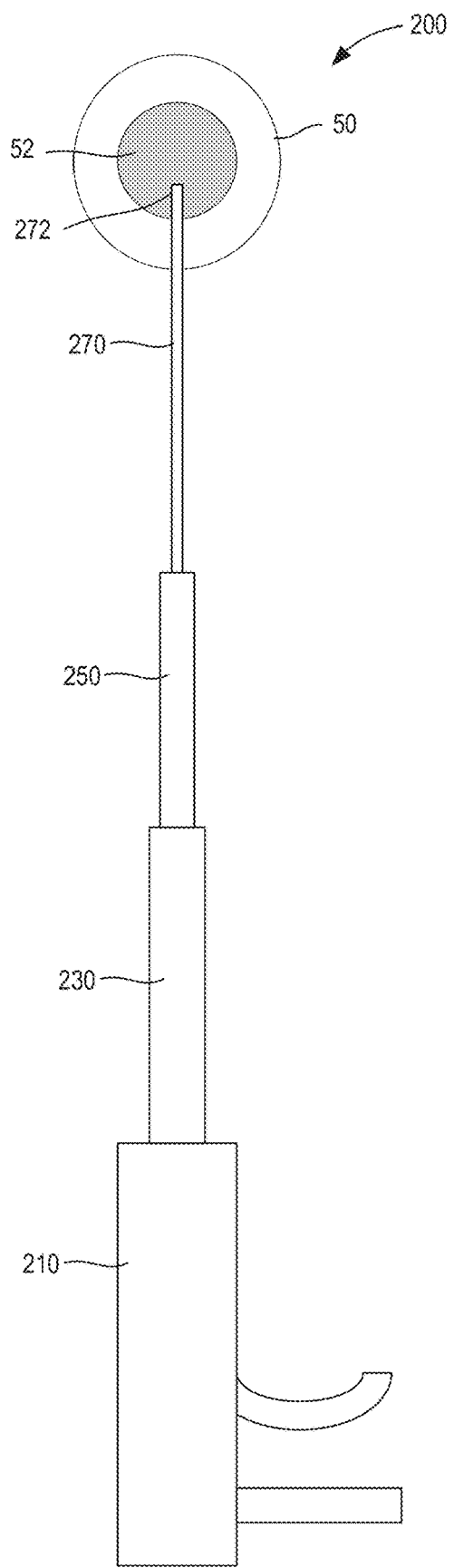
FIG. 2 is a top plan view of a hydrogel delivery assembly according to an embodiment.

Referring to FIG. 2, a hydrogel delivery assembly 200 ("assembly 200") is shown according to another embodiment. The assembly 200 can be for use in the kits and methods of the present disclosure. In some embodiments, the assembly 200 is provided in a kit that may be used to repair or supplement the nucleus pulposus of a patient in need thereof. In some embodiments, aspects, portions, and/or functions of the assembly 200 can be similar to and/or substantially the same as aspects, portions, and/or functions of the assembly 100, described above with reference to FIG. 1. Accordingly, such aspects, portions, and/or functions of the assembly 200 are not described in further detail herein.

As shown in FIG. 2, the assembly 200 includes an injector 210 that is coupled to a syringe 230 and a needle 270. The assembly 200 is configured for injection of a hydrogel of the present disclosure into a nucleus pulposus 52 of a vertebral disc 50. In some embodiments, the injector 210 can include and/or can form a housing that can receive at least a portion of the syringe 230. In some embodiments, the injector 210 (e.g., a base, a housing, a holder, etc.) can include an actuator and/or other suitable mechanism configured to manipulate the syringe 230 to expel the hydrogel contained in the syringe 230.

In some embodiments, prior to injection, a hydrogel of the present disclosure is heated to about 121° C. in an autoclave and inserted into syringe 230. In some embodiments, syringe 230 is pre-packed with a hydrogel of the present disclosure and the hydrogel-containing syringe 230 is heated to the melting point of the hydrogel (e.g., between about 90° C. and about 121° C.) and the temperature is maintained at a desired injection temperature (e.g., between about 40° C. and about 90° C., as described above). A heating coil and/or any other suitable heating device is optionally wrapped around the exterior of syringe 230 to maintain temperature of the hydrogel in the syringe barrel 230.

A flexible extension tubing 250 can optionally be connected to the discharge end of the syringe 230 (e.g., between the syringe 230 and the needle 270). In some embodiments, the flexible extension tubing 250 is constructed from a medical grade polymer, such as polyurethane or any of the polymers described above. In some embodiments, the flexible extension tubing 250 is about 160 mm long and has an inner diameter of about 1.59 mm. In some embodiments, the flexible extension tubing 250 is about 10 inches long. In some embodiments, the flexible extension tubing 250 is about 6 inches long. However, those skilled in the art will recognize that the tubing 250 can be other lengths and/or inner diameters. The flexibility of the flexible extension tubing 250 may provide the surgeon with a degree of freedom and may allow the surgeon to move around during the hydrogel injection process without moving the delivery needle inserted into the nucleus, enabling the surgeon to monitor the injection process through a real-time fluoroscopy without exposing the operator's hands to unnecessary radiation. In some embodiments, the assembly 200 need not include a flexible extension tubing 250 (e.g., the needle 270 is connected to the discharge end of the syringe 230 without the flexible extension tubing 250 disposed therebetween). In some embodiments, the flexible extension tubing 250 is not present.

The needle 270 has a discharge end 272 that is inserted through the wall of the disc 50 into the nucleus pulposus 52 for injection of the hydrogel. In some embodiments, the needle 270 is a 20 gauge needle. In other embodiments, the gauge of the needle 270 is selected from the group consisting of about 15 gauge, about 16 gauge, about 17 gauge, about 18 gauge, about 19 gauge, about 20 gauge, about 21 gauge, and about 22 gauge. In other embodiments, the gauge of the needle 270 is greater than about 17 gauge, such as about 16 gauge or about 15 gauge. Fine gauge needles can reduce and/or can substantially minimize the size of the injection opening through the wall of the disc 50, thereby reducing and/or substantially minimizing the size of the opening through which the hydrogel can escape from the disc 50 after the needle 270 is removed from the disc 50 following injection (e.g., relative to the use of larger-gauge needles).

The assembly 200 can be used to inject a desired volume (e.g., between about 0.1 cc to about 12.0 cc) of hydrogel of the present disclosure into the nucleus pulposus 52 in a manner similar to that described above with reference to the assembly 100.

FIGS. 3-7B illustrate a hydrogel delivery assembly 300 according to another embodiment. The hydrogel delivery assembly 300 ("assembly 300") can be used to inject any of the hydrogels described herein into a nucleus pulposus of a vertebral disc to provide for augmentation, repair, and/or replacement thereof. In some embodiments, aspects, portions, and/or functions of the assembly 300 can be similar to and/or substantially the same as aspects, portions, and/or functions of the assembly 100 and/or 200, described in detail above with reference to FIG. 1 and FIG. 2, respectively. Accordingly, such aspects, portions, and/or functions of the assembly 300 may not be described in further detail herein.

Figure 3:
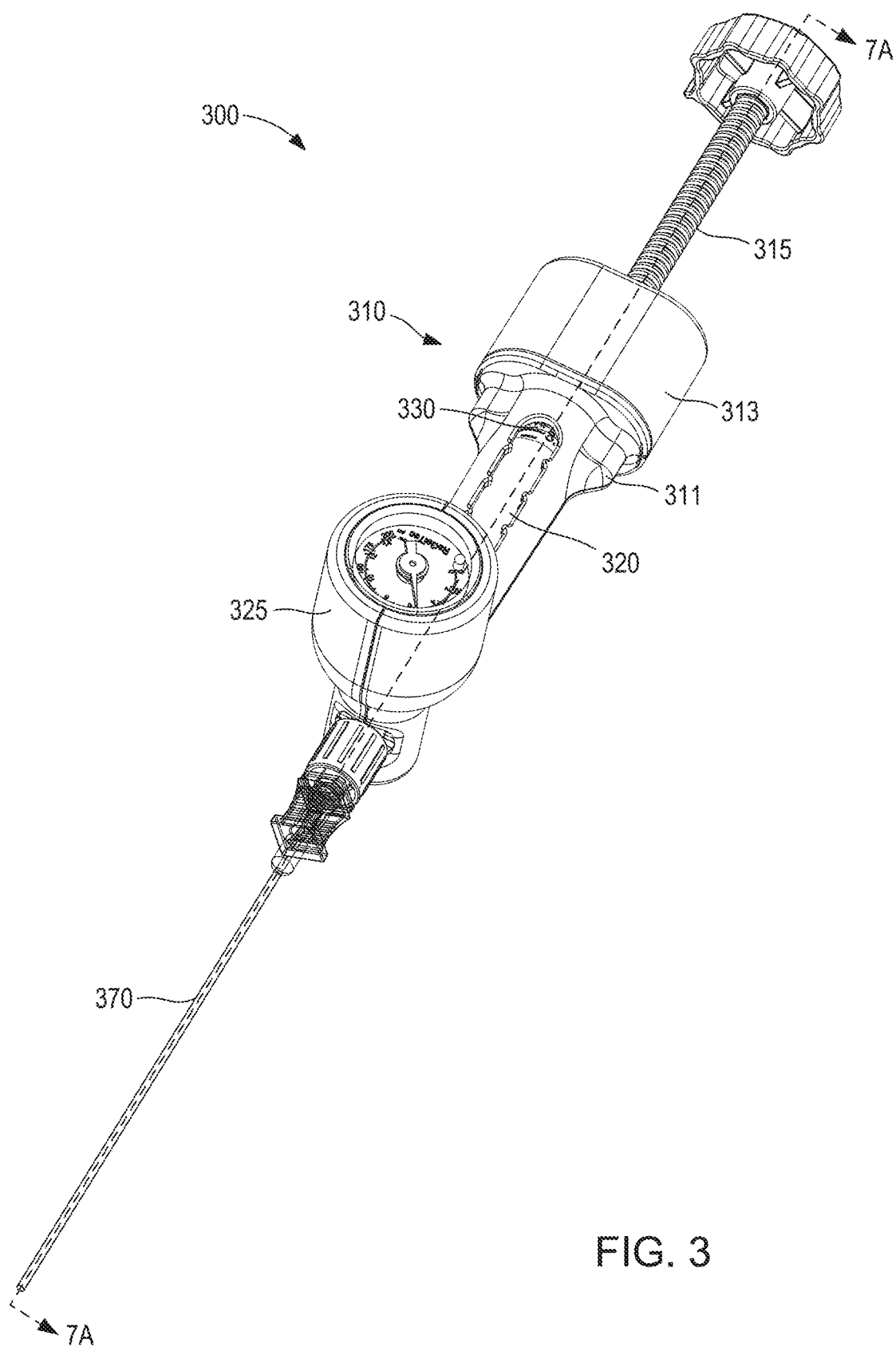
FIG. 3 is a perspective view of a hydrogel delivery assembly according to an embodiment.
Figure 4:
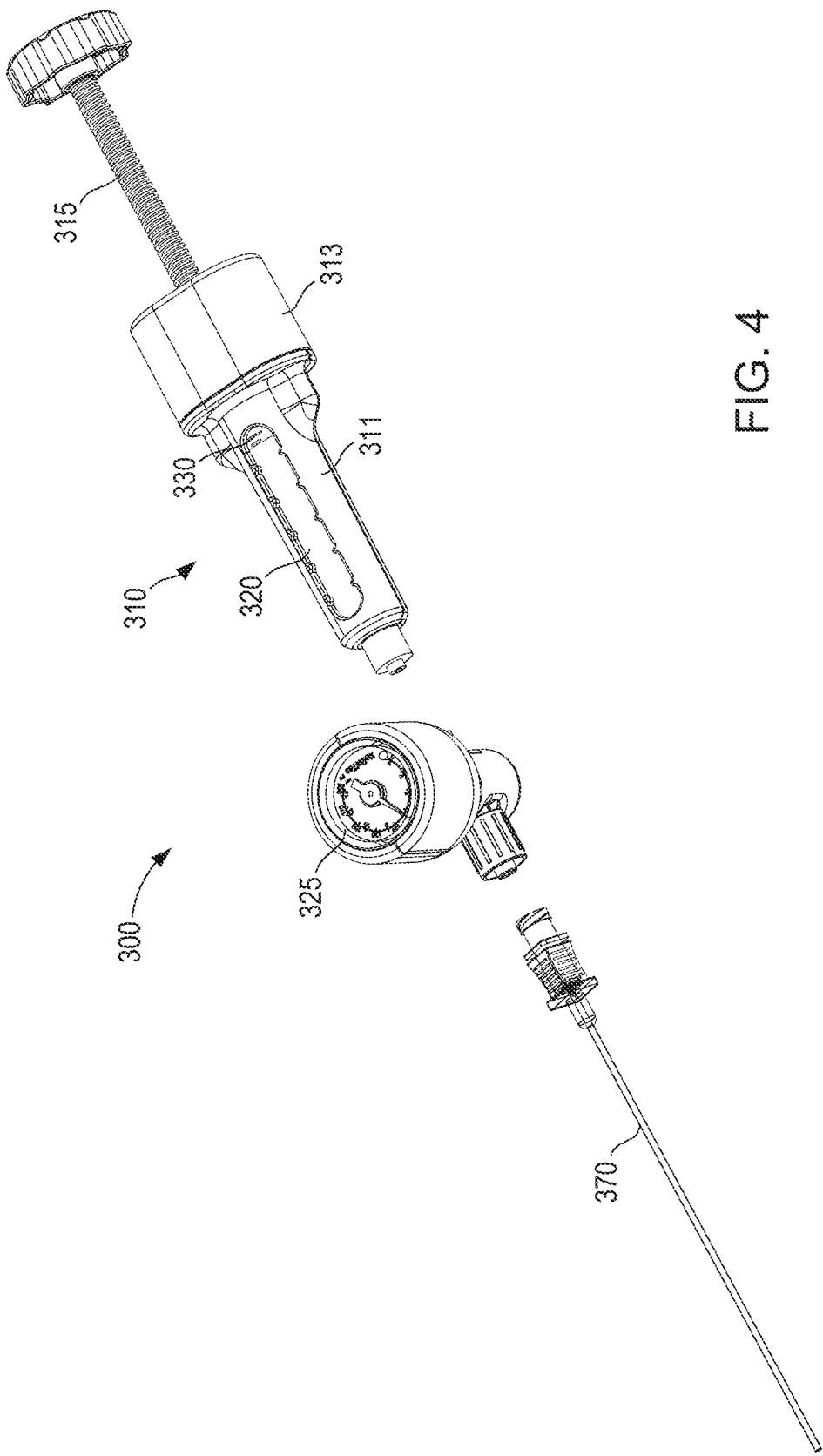
FIG. 4 is a partial exploded perspective view of the hydrogel delivery assembly of FIG. 3.

As shown in FIGS. 3 and 4, the assembly 300 includes at least an injector 310, a syringe 330, a heater assembly 320, a pressure gauge assembly 325, and a needle 370. While the components of the assembly 300 are shown as being arranged in a specific configuration, it should be understood that the arrangement of the assembly 300 shown in FIGS. 3 and 4 is presented by way of example only and not limitation. For example, while certain components of the assembly 300 are shown in a particular order and/or are shown coupled in a particular manner, it should be understood that other arrangements are possible. A discussion of the components of the assembly 300 is provided below followed by a discussion of a method of using the assembly 300 to inject any of the hydrogels described herein into a nucleus pulposus of a vertebral disc.

Figure 5:
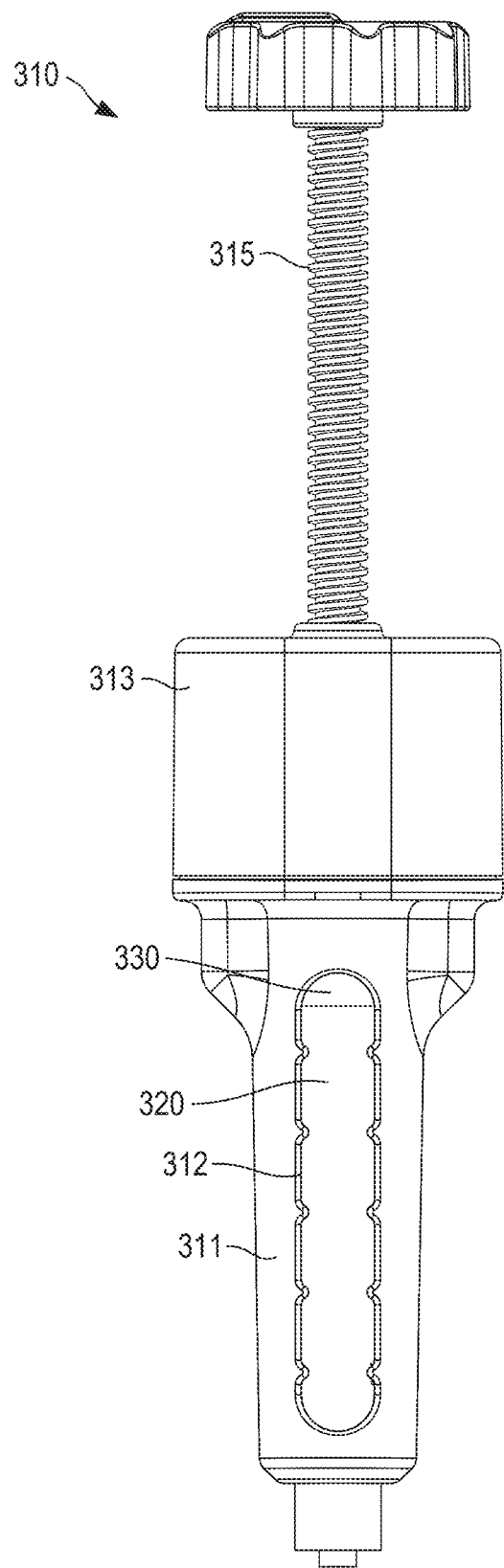
FIG. 5 is a front view of a hydrogel delivery device included in the hydrogel delivery assembly of FIG. 3.

The injector 310 of the assembly 300 can be any suitable shape, size, and/or configuration. For example, in some embodiments, the injector 310 can be similar to the injectors 110 and/or 210 described in detail above. As shown in FIGS. 5 and 6, the injector 310 is configured to receive, house, and/or contain at least a portion of the syringe 330, the heater assembly 320, and an actuator 315. For example, the injector 310 includes a sleeve 311 that is removably coupleable to a cap 313. The sleeve 311 and the cap 313 collectively define an inner volume within which at least a portion of the syringe 330, the heater assembly 320, and the actuator 315 can be disposed. Moreover, the sleeve 311 defines one or more openings or windows configured to allow visualization of at least a portion of the components disposed in the inner volume (e.g., a portion of the syringe 330, heater assembly 320, and/or actuator 315).

The sleeve 311 and the cap 313 can be coupled via any suitable coupling mechanism. For example, as shown in FIG. 6, the injector 310 can include a set of mechanical fasteners (e.g., a set of two screws) configured to removably couple the cap 313 to the sleeve 311. In other embodiments, the cap 313 can be removably coupled to the sleeve 310 via a threaded fitting, a friction fit, one or more latches, one or more tabs, etc. In some implementations, the removable coupling between the sleeve 311 and the cap 313 can allow a user to convey a volume of hydrogel into the syringe 330 while the syringe 330 is outside of the injector 310. After filling, the syringe 330 can then be loaded or inserted into the sleeve 311 and the cap 313 can be coupled to the sleeve 313. In other implementations, the syringe 330 can filled while disposed in the injector 310.

The injector 310 includes a bias member 317 coupled to and/or otherwise disposed in the cap 313 and configured to engage a portion of the syringe 330 to bias or otherwise maintain the syringe 330 in a desired position within the injector 310. For example, as shown in FIG. 6, the bias member 317 can be a spring or the like configured to engage and/or contact a proximal flange of the syringe 330. In some embodiments, the bias member 317 can exert a force of the syringe 330 (e.g., the proximal flange of the syringe 330) that is operable in placing and/or maintaining the syringe 330 in a distal position within the injector 310. For example, in some embodiments, the syringe 330 can be placed and/or maintained in a distal position such that a distal end portion (e.g., a lock, coupler, etc.) of the syringe 330 extends through an opening defined by the sleeve 311 (see e.g., FIG. 5).

While the bias member 317 is shown and described above being a spring, in other embodiments, the injector 310 can include any suitable bias member such as, for example, a relatively soft, compliant, and/or compressible member. In other embodiments, the injector 310 need not include a bias member. For example, the cap 313 can include one or more features, protrusions, shoulders, tabs, etc. configured to engage and/or contact the syringe 330. In still other embodiments, the coupling of the cap 313 to the sleeve 311 can be such that the proximal flange of the syringe 330 is captured opposing surfaces of the cap 313 and sleeve 311 that collectively retain the proximal flange of the sleeve 330 in a fixed position relative thereto. In some implementations, biasing and/or otherwise maintaining the syringe 330 in a desired and/or fixed position within the injector 310 can allow for actuation of the injector 310 operable to expel the hydrogel from the syringe 330, as described in further detail herein.

The actuator 315 of the injector 310 is configured to actuate and/or manipulate a portion of the syringe 330 disposed within the injector 310. The actuator 315 can be any suitable member, device, assembly, mechanism, etc. configured to actuate and/or manipulate the portion of the syringe 330 (e.g., either directly or indirectly). For example, in some embodiments, the actuator 315 can be and/or can include a plunger, a push rod, a rotationally actuated rod, a lever, a trigger and/or ratchet mechanism, a pumping mechanism, and/or any other suitable actuator. More specifically, in this embodiment, the actuator 315 is a threaded actuator rod or the like.

As shown in FIGS. 5 and 6, the actuator 315 has a first end portion (e.g., a proximal end portion) that is configured to be disposed outside of the inner volume defined by the sleeve 311 and the cap 313, and a second end portion (e.g., a distal end portion) that is configured to be inserted into and/or through the cap 313 to be disposed within the inner volume. The first end portion of the actuator 315 includes and/or forms a handle, knob, and/or engagement feature configured to be engaged by a user. The second end portion includes and/or is coupled to a plunger 316 that is disposed or configured to be disposed within the syringe 330.

The cap 313 can include and/or can be coupled to an anchor member 314 and/or the like that can be configured to selectively engage a portion of the actuator 315 disposed in the inner volume. For example, the anchor member 314 can be a nut or threaded coupler configured to receive a portion of the actuator 315 to define a threaded coupling therebetween. In some embodiments, the anchor member 314 is fixedly coupled to the cap 313 such that rotation of the actuator 315 about a longitudinal axis results in a linear advancement of the actuator 315 along the longitudinal axis. As described in further detail herein, with the second end portion of the actuator 315 coupled to and/or otherwise including the plunger 316, the linear advancement of the actuator 315 in the direction of and/or otherwise along its longitudinal axis is operable to advance the plunger 316 within the syringe 330. More specifically, the actuator 315 can be rotated in a direction that results in advancement of the actuator 315 in a distal direction, which in turn results in movement of the plunger 316 within the syringe 330 that is operable to expel at least a portion of the hydrogel contained therein.

The syringe 330 can be any suitable syringe or any other suitable reservoir. For example, the syringe 330 can be similar to and/or substantially the same as the syringes 130 and/or 230 described in detail above. In some embodiments, the syringe 330 can sized and/or configured to at least temporarily contain a volume of a hydrogel composition between about 0.1 cc to about 12.0 cc, as described above. The syringe 330 can be formed from any suitable material such as, for example, any of the biocompatible materials described above. In some embodiments, the syringe 330 can be formed of a material that is configured to withstand, tolerate, and/or otherwise be compatible with temperatures sufficient to maintain the hydrogel composition in a substantially viscous state (e.g., between about 40° C. and about 90° C.). In some embodiments, the syringe 330 can be formed of a material that is compatible with temperatures associated with an initial heating of the hydrogel prior to being conveyed into the syringe 330 (e.g., about 121° C. or more). In some embodiments, the syringe 330 can be formed from a material with a thermal conductivity that can allow the syringe 330 to transfer thermal energy received (e.g., directly or indirectly) from the optional heater assembly 320 to the hydrogel contained within the syringe 330.

The heater assembly 320 can be any suitable heating device or the like. For example, in some embodiments, the heater assembly 320 can be and/or can include an electric heater (e.g., configured to receive AC electric power or DC electric power). The heater assembly 320 is configured to be disposed in the inner volume collectively defined by the sleeve 311 and the cap 313. In some embodiments, the heater assembly 320 is disposed in the sleeve 311 of the injector 310 such that the heater assembly 320 at least partially wraps around and/or otherwise at least partially surrounds a portion of the syringe 330. For example, as shown in FIGS. 5 and 6, the heater assembly 320 is a sleeve or the like in or through which the syringe 330 can be inserted. In some embodiments, the heater assembly 320 can be in contact with a surface of the syringe 330 to allow for direct thermal contact and/or direct thermal transfer therebetween. In other embodiments, the heater assembly 320 can be positioned adjacent to but not in contact with the syringe 330, resulting in indirect thermal contact and/or indirect thermal transfer therebetween.

As described above, the assembly 300 also includes a pressure gauge assembly 325 and a needle 370 that can be coupled to and/or in fluid communication with a portion of the injector 310. For example, referring back to FIGS. 3 and 4, the pressure gauge assembly 325 can be coupled to the distal or discharge end portion of the syringe 330 (e.g., via a luer connection or any other suitable coupling). The pressure gauge assembly 325 can be any suitable pressure gauge, monitor, regulator, and/or the like. In this embodiment, the pressure gauge assembly 325 is coupled between the distal or discharge end portion of the syringe 330 and a proximal end portion of the needle 370. In this manner, the pressure gauge assembly 325 can be configured to determine, monitor, test, regulate, and/or indicate a backpressure associated with and/or resulting from injection of the hydrogel into the nucleus pulposus of the disc. As described above, in some implementations, a desirable amount of backpressure can be between about 35 psi and about 300 psi.

As shown in FIG. 3, the needle 370 has a proximal end portion that is coupled to a distal or discharge end portion of the pressure gauge assembly 325 (e.g., via a luer connection and/or any other suitable coupling). The needle 370 has a distal or discharge end portion that is configured for insertion into a patient, through a wall of a vertebral disc, and into the nucleus pulposus for injection of the hydrogel. In some embodiments, the needle 370 can be between a 15 gauge needle and a 22 gauge needle. In other embodiments, the gauge of the needle 370 is greater than 15 gauge (e.g., 12 gauge, 11 gauge, 10 gauge, etc.) or less than 22 gauge (e.g., 24 gauge, 26 gauge, 27 gauge, etc.). In some instances, the use of a fine gauge needle 370 (e.g., 15 gauge or smaller) can reduce and/or can substantially minimize the size of the injection opening through the wall of the disc, thereby reducing and/or substantially minimizing the size of the opening through which the hydrogel can escape from the disc after the needle 370 is removed from the disc following injection (e.g., relative to the use of larger-gauge needles). In some implementations, the size or gauge of the needle 370 can be selected and/or at least partially based on a desired amount of backpressure, a desired hydrogel flowrate, a desired amount of time to deliver a therapeutically effective amount of hydrogel, one or more patient characteristics (e.g., age, physical condition, etc.), and/or any other practical considerations.

Figure 7A:
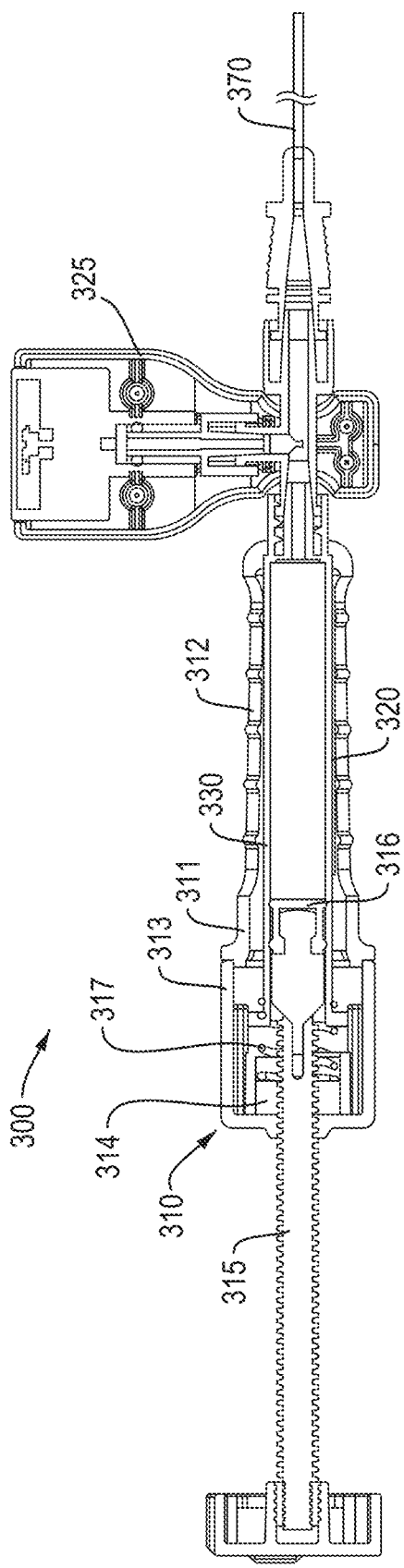
FIG. 7A and FIG. 7B are cross-sectional views of the hydrogel delivery assembly of FIG. 3, taken along the line 7A-7A, and shown in a first configuration and a second configuration, respectively.
Figure 7B:
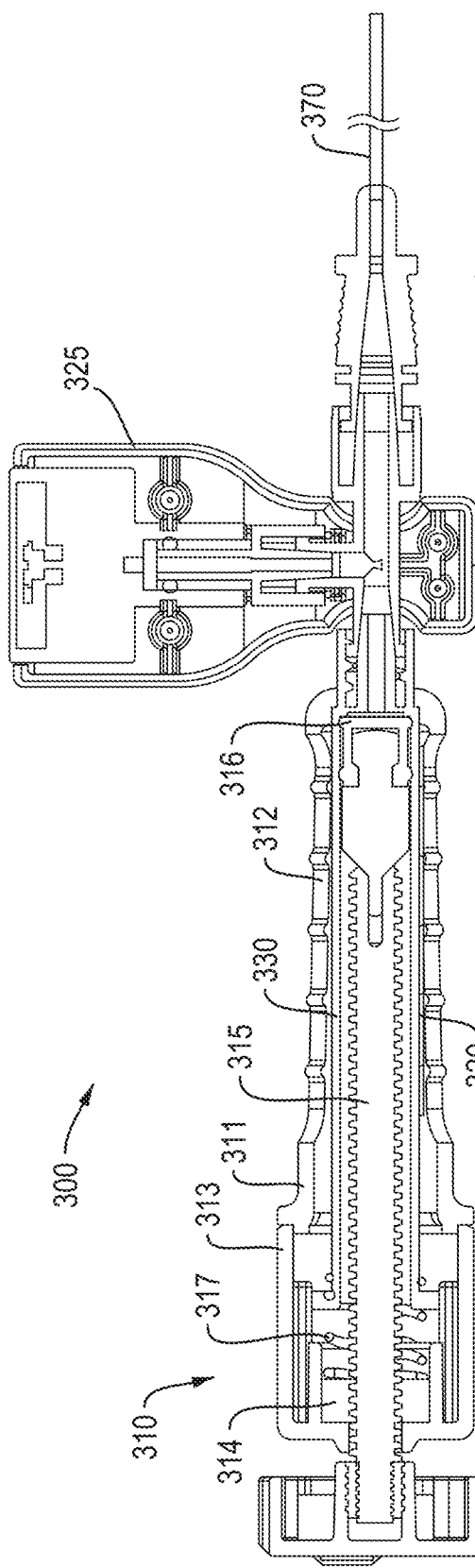

As described above, the assembly 300 can be used to inject any of the hydrogels described herein into a nucleus pulposus of a vertebral disc to provide for augmentation, repair, and/or replacement thereof. For example, FIGS. 7A and 7B illustrate the assembly 300 in a first configuration and a second configuration, respectively. In some implementations, a method of using the assembly 300 can include heating a hydrogel of the present disclosure to about 121° C. in an autoclave and conveyed into the syringe 330. With the heated hydrogel disposed in the syringe 330, the syringe 330 can be positioned within the inner volume collectively defined by the sleeve 311 and the cap 313. As described above, the bias member 317 can be configured to contact and/or otherwise engage the syringe 330 to place and/or substantially maintain the syringe 330 in a distal position within the injector 310. Moreover, the actuator 315 can be in a first configuration and/or state in which the plunger 316 is in a proximal position relative to the syringe 330.

The heater assembly 320 is also disposed in the inner volume of the injector 310 and can be activated (e.g., by receiving electric power or other form of activation) to transfer thermal energy to the hydrogel contained in the syringe 330. As described in detail above, in some implementations, the heater assembly 320 can transfer thermal energy to the hydrogel to maintain the hydrogel at a desired injection temperature between about 40° C. and about 90° C.

As described above, a proximal or inlet end portion of the pressure gauge assembly 325 can be physically and fluidically coupled to the distal end portion of the syringe 330 when the syringe 330 is disposed in the injector 310. In addition, the proximal or inlet end portion of the needle 370 can be physically and fluidically coupled to the distal or discharge end of the pressure gauge assembly 325. Thus, a fluid flow path is defined between an inner volume of the syringe 330 and a lumen defined by the needle 330. In this manner, the assembly 300 can be in its first configuration and/or state, as shown in FIG. 7A.

With the assembly 300 in the first configuration, a user (e.g., a surgeon, doctor, interventional radiologist or technician, etc.) can manipulate the assembly 300 to insert the distal or discharge end portion of the needle 370 through bodily tissue of the patient, through a wall of a vertebral disc, and into the nucleus pulposus of the disc. Once inserted, the actuator 315 can be actuated and/or otherwise transitioned from its first configuration or state to its second configuration and/or state. For example, a user can rotate the actuator 315 relative to the cap 313 and/or sleeve 311, which in turn, advances the actuator 315 along its longitudinal axis in a distal direction. The actuator 315 can be actuated (e.g., rotated) to inject at least a portion of the hydrogel contained in the syringe 330 into the disc. In some implementations, a therapeutically effective amount of hydrogel to inject into the nucleus pulposus can be between about 0.1 cc and about 12.0 cc. Moreover, during the injection, the pressure gauge assembly 325 can be used to monitor a backpressure associated with the flow of the hydrogel into the disc. As shown in FIG. 7B, conveying the therapeutically effective amount of hydrogel to the disc places the assembly 300 in its second configuration and/or state. With the hydrogel injected in the disc and with the assembly 300 in its second configuration, the needle 370 can be removed from the patient.

Method of Making Hydrogel:

In one aspect, the present disclosure provides methods of making the hydrogels of the present disclosure. The manufacturing methods provided herein provide hydrogels of consistent quality, which is essential for a manufacturing process of a medical device.

In some embodiments, the method of manufacturing a hydrogel comprises:
(a) forming a mixture of at least one polymer and a solvent;
(b) stirring the mixture of step (a);
(c) melting the stirred mixture of step (b) to form a solution; and
(d) cooling the solution of step (c) to provide a hydrogel, wherein at a temperature of about 65° C. the hydrogel is capable of injection through a 16 cm length, 17 gauge needle at an injection rate of at least 2.0 cc per minute using an injection pressure of about 50 psi to provide a tissue implant having a Young's modulus of between about 0.1 to 5.0 MPa.

In some embodiments, the method of manufacturing a hydrogel comprises:
(a) forming a mixture of at least one polymer and a solvent;
(b) stirring the mixture of step (a);
(c) melting the stirred mixture of step (b) to form a solution; and
(d) cooling the solution of step (c) to provide a hydrogel, wherein at a temperature of about 65° C. the hydrogel is capable of safe injection into the nucleus of an intervertebral disc of a living patient through a 16 cm length, 17 gauge needle to provide a tissue implant having a Young's modulus of between about 0.1 to 5.0 MPa.

In some embodiments, at least one polymer is a mixture of polyvinyl alcohol, polyvinylpyrrolidone, polyethylene glycol and the solvent is water. In some embodiments, the mixture of step (a) further comprises a contrast agent. In some embodiments, the contrast agent is barium sulfate. In some embodiments, the contrast agent is silver sulfate.

In some embodiments, the mixture of step (a) consists essentially of:
(1) about 7 wt. % to about 17 wt. % of polyvinyl alcohol;
(2) about 0.07 wt. % to about 0.17% of polyvinylpyrrolidone;
(3) about 13 wt. % to about 23 wt. % of polyethylene glycol;
(4) about 3 wt. % to about 13 wt. % of a contrast agent and
(5) about 57 wt. % to about 67 wt. % of water.

In some embodiments, the mixture of step (a) consists essentially of:
(1) about 9 wt. % to about 15 wt. % of polyvinyl alcohol;
(2) about 0.09 wt. % to about 0.15% of polyvinylpyrrolidone;
(3) about 15 wt. % to about 21 wt. % of polyethylene glycol;
(4) about 5 wt. % to about 11 wt. % of a contrast agent and
(5) about 59 wt. % to about 65 wt. % of water.

In some embodiments, the mixture of step (a) consists essentially of:
(1) about 11 wt. % to about 13 wt. % of polyvinyl alcohol;
(2) about 0.11 wt. % to about 0.13% of polyvinylpyrrolidone;
(3) about 17 wt. % to about 19 wt. % of polyethylene glycol;
(4) about 7 wt. % to about 9 wt. % of a contrast agent and
(5) about 61 wt. % to about 63 wt. % of water.

In some embodiments, the present disclosure provides a method of manufacturing a hydrogel comprising:
(1) about 12 wt. % to about 22 wt. % of polyvinyl alcohol;
(2) about 0.12 wt. % to about 0.22 wt. % of polyvinylpyrrolidone;
(3) about 12 wt. % and about 22 wt. % polyethylene glycol; and
(4) a solvent, the method comprising:
(a) forming a mixture of polyvinyl alcohol, polyvinylpyrrolidone, polyethylene glycol and a solvent;
(b) stirring the mixture of step (a);
(c) melting the stirred mixture of step (b) to form a solution; and
(d) cooling the solution of step (c).

In some embodiments, the present disclosure provides a method of manufacturing a hydrogel, the method comprising:
(a) forming a mixture comprising PVA, PVP and water;
(b) heating the mixture of Step (a) to form a solution;
(c) heating polyethylene glycol having a Mw of about 800 Da to about 2,000 Da;
(d) adding the heated PEG from step (c) to the heated mixture of step (b);
(e) cooling the mixture of step (d) to provide a hydrogel;
(f) conducting a phase separation to provide an aqueous supernatant and a hydrogel; and
(g) removing the aqueous supernatant to provide the hydrogel.

In some embodiments, the heating of step (b) is from about 80° C. to about 135° C., including about 80° C., about 90° C., about 100° C., about 110° C., about 120° C., about 130° C. and about 135° C., including all ranges and values there between. In some embodiments, the heating of step (b) is from about 95° C. to about 120° C.

In some embodiments, the heating of step (c) is from about 80° C. to about 135° C., including about 80° C., about 90° C., about 100° C., about 110° C., about 120° C., about 130° C. and about 135° C., including all ranges and values there between. In some embodiments, the heating of step (c) is from about 95° C. to about 120° C.

In some embodiments, the phase separation is conducted by centrifugation. In some embodiments, the centrifugation is conducted at a speed and for a time that is sufficient to achieve phase separation but does not form a density gradient of suspended contrast agent.

In some embodiments, the centrifugation is conducted at from about 3,000 g to about 7,000 g, including about 3,000 g, about 3,500 g, about 4,000 g, about 4500 g, about 5000 g, about 6,000 g, about 6,500 g, and about 7,000 g, including all values and ranges therebetween. In some embodiments, the centrifugation is conducted at from about 4,000 g to about 6,000 g. In some embodiments, the centrifugation is conducted for from about 5 min to about 10 min. In some embodiments, the centrifugation is conducted at from about 4,000 g to about 6,000 g for from about 5 min to about 10 min. In some embodiments, the centrifugation is conducted at about 4,300 g for about 10 min.

In some embodiments, the mixture of step (a) further comprises a contrast agent. In some embodiments, the contrast agent is silver nitrate. In some embodiments, wherein the contrast agent is barium sulfate.

In some embodiments, the mixture of step (e) comprises:
about 7 wt. % to about 17 wt. % of polyvinyl alcohol;
about 0.07 wt. % to about 0.17% of polyvinylpyrrolidone;
about 13 wt. % to about 23 wt. % of polyethylene glycol;
about 3 wt. % to about 13 wt. % of barium sulfate and
about 57 wt. % to about 67 wt. % of water.

In some embodiments, the mixture of step (e) comprises:
about 9 wt. % to about 15 wt. % of polyvinyl alcohol;
about 0.09 wt. % to about 0.15% of polyvinylpyrrolidone;
about 15 wt. % to about 21 wt. % of polyethylene glycol;
about 5 wt. % to about 11 wt. % of barium sulfate and
about 59 wt. % to about 65 wt. % of water.

In some embodiments, the mixture of step (e) comprises:
about 11 wt. % to about 13 wt. % of polyvinyl alcohol;
about 0.11 wt. % to about 0.13% of polyvinylpyrrolidone;
about 17 wt. % to about 19 wt. % of polyethylene glycol;
about 7 wt. % to about 9 wt. % of barium sulfate and
about 61 wt. % to about 63 wt. % of water.

In some embodiments, the hydrogel does not contain a chemically cross-linked polymer.

In some embodiments, the polyethylene glycol is non-functionalized polyethylene glycol. In some embodiments, the non-functionalized polyethylene glycol has an Mw of about 800 Da to about 1,200 Da. In some embodiments, the non-functionalized polyethylene glycol has a Mw of about 900 Da to about 1,100 Da. In some embodiments, the non-functionalized polyethylene glycol has a Mw of about 1,000 Da.

In some embodiments,
the polyvinyl alcohol has an Mw of about 135,000 Da to about 155,000 Da;
the non-functionalized polyethylene glycol has an Mw of about 800 Da to about 1,200 Da; and
the polyvinylpyrrolidone has an Mw of about 35,000 Da to about 45,000 Da.

In some embodiments, methods of the present disclosure provide a hydrogel having a viscosity about 10 Pa·s at a temperature of about 65° C. In some embodiments, methods of the present disclosure provide a hydrogel having a viscosity of 8±2 Pa·s at a temperature of about 65° C.

In some embodiments, methods of the present disclosure provide a hydrogel having a Young's modulus of about 0.25 MPa. In some embodiments, methods of the present disclosure provide a hydrogel having a Young's modulus of 0.2±0.05 MPa.

In some embodiments, the present disclosure provides hydrogels prepared according to the methods described herein.

Implants:

In one aspect, the present invention provides a tissue implant having a Young's modulus of between about 0.1 to 5.0 MPa, wherein the tissue implant is formed by the injection of a hydrogel the present disclosure into a living patient's tissue. The tissue implants of the present disclosure are suitable to repair and supplement a variety of tissues, including repair of damaged articular cartilage, bulking agent to support the urethra (for the treatment of incontinence or vesicoureteral reflux), repair or replacement of the nucleus pulposus of an intervertebral disc and a filler for use in cosmetic applications. In some embodiments, the tissue implants of the present disclosure are suitable to repair and replace the nucleus pulposus of an intervertebral disc.

In some embodiments, the tissue implants of the present disclosure have a Young's modulus of between about 0.1 to 5.0 MPa, and the tissue implant is formed by the injection of a hydrogel into a living patient's tissue, wherein the hydrogel comprises:
at least one polymer; and
a solvent,
wherein at a temperature of about 65° C. the hydrogel is capable of injection through a 16 cm length, 17 gauge needle at an injection rate of at least 2.0 cc per minute using an injection pressure of about 50 psi.

In some embodiments, the tissue implants of the present disclosure have a Young's modulus of between about 0.1 to 5.0 MPa, and the tissue implant is formed by the injection of a hydrogel into the nucleus of an intervertebral disc of a living patient, wherein the hydrogel comprises:
at least one polymer; and
a solvent,
wherein at a temperature of about 65° C. the hydrogel is capable of safe injection into the nucleus of an intervertebral disc of a living patient.

In some embodiments, the tissue implants of the present disclosure have a Young's modulus of between about 0.1 to 5.0 MPa, and the tissue implant is formed by the injection of a hydrogel into the nucleus of an intervertebral disc of a living patient, wherein the hydrogel comprises:
at least one polymer; and
a solvent,
wherein at a temperature of about 65° C. the hydrogel is capable of safe injection into the nucleus of an intervertebral disc of a living patient through a 16 cm length, 17 gauge needle at an injection rate of at least 1.0 cc per minute, wherein the backpressure during the injection is from about 60 psi to about 200 psi.

In some embodiments, the tissue implants of the present disclosure have a Young's modulus of between about 0.1 to 5.0 MPa, and the tissue implant is formed by the injection of a hydrogel into a living patient's tissue, wherein the hydrogel comprises:
about 12 wt. % to about 22 wt. % of polyvinyl alcohol;
about 0.12 wt. percent to about 0.22 wt. % of polyvinylpyrrolidone;
about 12 wt. % and about 22 wt. % polyethylene glycol; and
a solvent.

In some embodiments, the tissue implants of the present disclosure have a Young's modulus of between about 0.1 to 5.0 MPa, and the tissue implant is formed by the injection of a hydrogel into a living patient's tissue, wherein the hydrogel comprises:
about 12 wt. % to about 22 wt. % of polyvinyl alcohol;
about 0.12 wt. percent to about 0.22 wt. % of polyvinylpyrrolidone;
about 12 wt. % and about 22 wt. % polyethylene glycol; and
a solvent,
wherein at a temperature of about 65° C. the hydrogel is capable of injection through a 16 cm length, 17 gauge needle at an injection rate of at least 2.0 cc per minute using an injection pressure of about 50 psi.

In some embodiments, the tissue implants of the present disclosure have a Young's modulus of between about 0.1 to 5.0 MPa, and the tissue implant is formed by the injection of a hydrogel into the nucleus of an intervertebral disc of a living patient, wherein the hydrogel comprises:
about 12 wt. % to about 22 wt. % of polyvinyl alcohol;

about 0.12 wt. percent to about 0.22 wt. % of polyvinylpyrrolidone;
about 12 wt. % and about 22 wt. % polyethylene glycol; and
a solvent,
wherein at a temperature of about 65° C. the hydrogel is capable of safe injection into the nucleus of an intervertebral disc of a living patient.

In some embodiments, the tissue implants of the present disclosure have a Young's modulus of between about 0.1 to 5.0 MPa, and the tissue implant is formed by the injection of a hydrogel into the nucleus of an intervertebral disc of a living patient, wherein the hydrogel comprises:
about 12 wt. % to about 22 wt. % of polyvinyl alcohol;
about 0.12 wt. percent to about 0.22 wt. % of polyvinylpyrrolidone;
about 12 wt. % and about 22 wt. % polyethylene glycol; and
a solvent,
wherein at a temperature of about 65° C. the hydrogel is capable of safe injection into the nucleus of an intervertebral disc of a living patient through a 16 cm length, 17 gauge needle at an injection rate of at least 1.0 cc per minute, wherein the backpressure during the injection is from about 60 psi to about 200 psi.

In some embodiments, the Young's modulus of the implant is about 0.1 MPa to about 5 MPa, including about 0.5 MPa, about 1.0 MPa, about 1.5 MPa, about 2.0 MPa, about 2.5 MPa, about 3.0 MPa, about 3.5 MPa, about 4.0 MPa, and about 4.5 MPa, and all ranges there in between. In certain embodiments, the Young's modulus of the implant is about 1.0 MPa to about 2.0 MPa. In certain embodiments, the Young's modulus of the implant is about 0.1 MPa to about 1.0 MPa.

In some embodiments, the Young's modulus of the implant is about 0.1 MPa, about 0.5 MPa, about 1.0 MPa, about 1.5 MPa, about 2.0 MPa, about 2.5 MPa, about 3.0 MPa, about 3.5 MPa, about 4.0 MPa, about 4.5 MPa or about 5.0 MPa. In certain embodiments, Young's modulus of the implant is about 0.1 MPa. In certain embodiments, Young's modulus of the implant is about 0.5 MPa.

Methods of Use:

In one aspect, the present disclosure provides methods of repairing or supplementing a tissue by administering a therapeutically effective amount of a hydrogel of the present disclosure to a patient in need thereof to provide a tissue implant. The methods of the present disclosure are suitable to repair and supplement a variety of tissues, including to repair damaged articular cartilage, bulking to support the urethra (for the treatment of incontinence or vesicoureteral reflux), repairing or replacing the nucleus pulposus of an intervertebral disc and filling for cosmetic applications.

The hydrogels of the present disclosure may be injected into the patient tissue using any suitable hydrogel delivery device. In some embodiments, the hydrogels of the present disclosure are injected using hydrogel delivery devices described in U.S. Pat. No. 8,475,532, which is hereby incorporated by reference in its entirety. In some embodiments, the hydrogels of the present disclosure are injected using any of the hydrogel delivery devices and/or assemblies described herein. In some embodiments, the hydrogels of the present disclosure are injected using a surgical robot (such as, the da Vinci Surgical system, Medtronic Mazor X Stealth Edition Surgical robot for spinal surgery and the Verb Surgical robot system).

In some embodiments, the method of repairing or supplementing a tissue in a patient in need thereof, comprises (a) melting a hydrogel of the present disclosure in a container;
(b) heating the mixture of step (a) to from about 60° C. to about 80° C.;
(c) inserting a 15 gauge or smaller needle into the tissue in need of repair or supplement;
(d) connecting the needle to the container; and
(e) injecting a therapeutically effective amount of the step (b) mixture into the tissue to provide a tissue implant having a Young's modulus of between about 0.1 to 5.0 MPa.

In some embodiments, the method of repairing or supplementing a tissue in a patient in need thereof, comprises (a) heating a hydrogel of the present disclosure in a container to about 120° C.;
(b) allowing the mixture of step (a) to cool to about 60° C. to about 80° C.;
(c) inserting a 15 gauge or smaller needle into the tissue in need of repair or supplement;
(d) connecting the needle to the container; and
(e) injecting a therapeutically effective amount of the step (b) mixture into the tissue to provide a tissue implant having a Young's modulus of between about 0.1 to 5.0 MPa.

As known to those skilled in the art, during the injection of a heated material through a needle, the injected material cools as it flows from the container, through the needle and into the patient's tissue (such as performed in step (e), above). Thus, depending on the delivery device configuration (e.g., needle length, needle insulation or needle heating, etc.), persons skilled in the art can determine a suitable temperature for the heating step (b) that accounts for the cooling during the injection and provides a safe temperature at the injection site (i.e., the patient's tissue). In some embodiments, the mixture of step (b) is heated to from about 60° C. to about 85° C., including about 60° C., about 65° C., about 70° C., about 75° C., about 80° C. and about 85° C., including all ranges there between. In some embodiments, the mixture of step (b) is heated to about 60° C., about 65° C., about 70° C., about 75° C., about 80° C. or about 85° C.

According to the methods of the present disclosure, the order of the steps of inserting the needle into the patient's tissue and connecting the needle to the hydrogel-containing container are reversible depending on the needs of the procedure.

The therapeutically effective amount of the hydrogel injected (also referred to as the therapeutically effective amount of the step (b) mixture) in the methods of the present disclosure depends on the tissue that is repaired or supplemented and may be determined by those of skill in the art.

In some embodiments, the therapeutically effective amount of hydrogel is determined by observing the implant in real time as it is injected using medical imaging (such as, fluoroscopy). In such embodiments, a therapeutically effective amount is the amount of hydrogel that is injected before the radiographic image shows that the gel is going into an undesirable location.

In some embodiments, the therapeutically effective amount of hydrogel is determined by the backpressure achieved during the injection (i.e., the hydrogel is injected until a pre-determined backpressure is reached). In some embodiments, the therapeutically effective amount of hydrogel is determined by:

(a) injecting a hydrogel of the present disclosure to a pre-determined pressure (for example, from about 120 psi to about 200 psi) as determined by a pressure gauge on the delivery system;

(b) pausing the hydrogel injection;
(c) monitoring the pressure gauge for a pressure decrease below the pre-determined pressure;
(d) injecting additional hydrogel until the pre-determined pressure is achieved;
(e) repeating the steps (b)-(d) until the pressure decrease in less than about 10% of the pre-determined pressure.

In some embodiments, the pre-determined pressure is from about 100 psi to about 250 psi, including about 100 psi, about 110 psi, about 120 psi, about 130 psi, about 140 psi, about 150 psi, about 160 psi, about 170 psi, about 180 psi, about 190 psi, about 200 psi, about 210 psi, about 220 psi, about 230 psi, about 240 psi, and about 250 psi, and all ranges there in between. In some embodiments, the pre-determined pressure is from about 100 psi to about 200 psi. In some embodiments, the pre-determined pressure is about 100 psi, about 110 psi, about 120 psi, about 130 psi, about 140 psi, about 150 psi, about 160 psi, about 170 psi, about 180 psi, about 190 psi, about 200 psi, about 210 psi, about 220 psi, about 230 psi, about 240 psi, or about 250 psi.

In some embodiments, the steps (b)-(d) are repeated until the present decrease is less than about 15%, less than about 10%, or less than about 5% of the pre-determined pressure.

In some embodiments, the present disclosure provides methods of repairing or supplementing the nucleus of an intervertebral disc in a patient in need thereof. In some embodiments, the method of repairing or supplementing the nucleus of an intervertebral disc in a patient in need thereof, comprises:
(a) melting a hydrogel of the present disclosure in a container;
(b) heating the step (a) mixture to from about 65° C. to about 80° C.;
(c) inserting a 15 gauge or smaller needle into the nucleus of an intervertebral disc in need of repair or supplement;
(d) connecting the needle to the container and
(e) injecting a therapeutically effective amount of the step (b) mixture into the nucleus of an intervertebral disc to provide a tissue implant,
wherein at a temperature of about 65° C. the hydrogel is capable of safe injection into the nucleus of an intervertebral disc of a living patient through a 16 cm length, 17 gauge needle at an injection rate of at least 1.0 cc per minute provide a tissue implant having a Young's modulus of between about 0.1 to 5.0 MPa, wherein the backpressure during the injection is from about 35 psi to about 300 psi.

In some embodiments, the backpressure during the injection of a therapeutically effective amount of the hydrogel into the nucleus of an intervertebral disc to provide a tissue implant having a Young's modulus of between about 0.1 to 5.0 MPa is from about 35 psi to about 300 psi, including about 40 psi, about 50 psi, about 60 psi, about 70 psi, about 80 psi, about 90 psi, about 100 psi, about 110 psi, about 120 psi, about 130 psi, about 140 psi, about 150 psi, about 160 psi, about 170 psi, about 180 psi, about 190 psi, about 200 psi, about 210 psi, about 220 psi, about 230 psi, about 240 psi, about 250 psi, about 260 psi, about 270 psi, about 280 psi, about 290 psi, and about 300 psi, and all ranges there in between. In certain embodiments, the backpressure during the injection of a therapeutically effective amount of the hydrogel into the nucleus of an intervertebral disc to provide a tissue implant having a Young's modulus of between about 0.1 to 5.0 MPa is from about 60 psi to about 200 psi. In certain embodiments, the backpressure during the injection of a therapeutically effective amount of the hydrogel into the nucleus of an intervertebral disc to provide a tissue implant having a Young's modulus of between about 0.1 to 5.0 MPa is from about 120 psi to about 200 psi.

In some embodiments, the method of repairing or supplementing the nucleus of an intervertebral disc in a patient in need thereof, comprises:
(a) melting a hydrogel of the present disclosure in a container;
(b) heating the step (a) mixture to from about 65° C. to about 80° C.;
(c) inserting a 15 gauge or smaller needle into the nucleus of an intervertebral disc in need of repair or supplement;
(d) connecting the needle to the container and
(e) injecting a therapeutically effective amount of the step (b) mixture into the nucleus of an intervertebral disc to provide a tissue implant,
wherein at a temperature of about 65° C. the hydrogel is capable of safe injection into the nucleus of an intervertebral disc of a living patient through a 16 cm length, 17 gauge needle at an injection rate of at least 1.0 cc per minute provide a tissue implant having a Young's modulus of between about 0.1 to 5.0 MPa, wherein the maximum backpressure during the injection is about 300 psi.

In some embodiments, the maximum backpressure during the injection of a therapeutically effective amount of the hydrogel into the nucleus of an intervertebral disc to provide a tissue implant having a Young's modulus of between about 0.1 to 5.0 MPa is less than about 60 psi, about 70 psi, about 80 psi, about 90 psi, about 100 psi, about 110 psi, about 120 psi, about 130 psi, about 140 psi, about 150 psi, about 160 psi, about 170 psi, about 180 psi, about 190 psi, about 200 psi, about 210 psi, about 220 psi, about 230 psi, about 240 psi, about 250 psi, about 260 psi, about 270 psi, about 280 psi, about 290 psi, or about 300 psi. In certain embodiments, the maximum backpressure during the injection of a therapeutically effective amount of the hydrogel into the nucleus of an intervertebral disc to provide a tissue implant having a Young's modulus of between about 0.1 to 5.0 MP is less than about 250 psi. In certain embodiments, the maximum backpressure during the injection of a therapeutically effective amount of the hydrogel into the nucleus of an intervertebral disc to provide a tissue implant having a Young's modulus of between about 0.1 to 5.0 MP is less than about 200 psi.

Figure 8A:
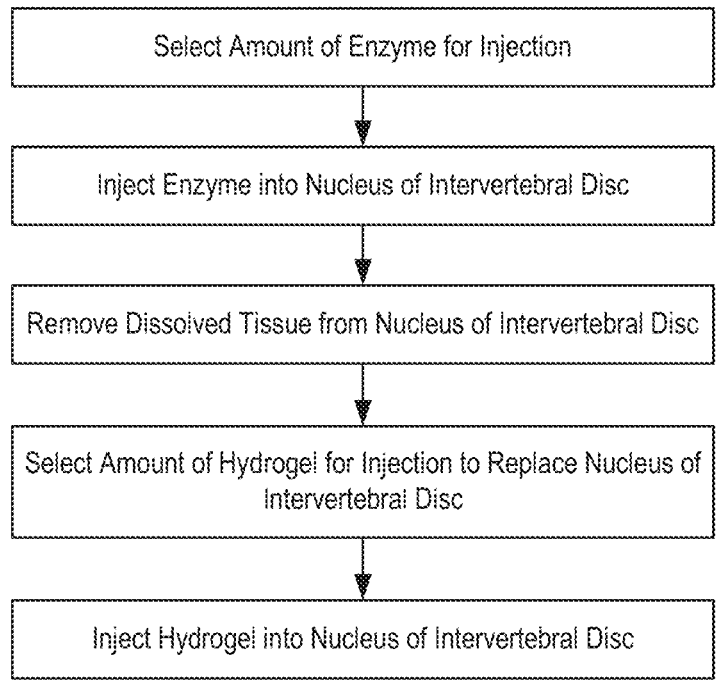
FIG. 8A shows a method of the present disclosure for replacing the nucleus of an intervertebral disc.
Figure 8B:
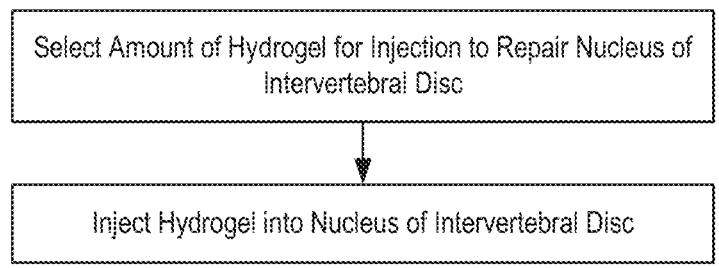
FIG. 8B shows a method of the present disclosure for repairing the nucleus of an intervertebral disc.

In some embodiments, the present disclosure provides a method for repairing a nucleus pulposus in a patient in need thereof (e.g., as shown in FIG. 8B). In some embodiments, the method for repairing a degenerated disc in a patient in need thereof comprises injecting about 0.1 cc to about 12.0 cc, including about 0.1 cc, about 0.5 cc, about 1.0 cc, about 1.5 cc, about 2.0 cc, about 2.5 cc, about 3.0 cc, about 3.5 cc, about 4.0 cc, about 4.5 cc, about 5.0 cc, about 5.5 cc, about 6.0 cc, about 6.5 cc, about 7.0 cc, about 7.5 cc, about 8.0 cc, about 8.5 cc, about 9.0 cc, about 9.5 cc, about 10.0 cc, about 10.5 cc, about 11.0 cc, about 11.5 cc and about 12.0 cc and all ranges there between, and all ranges there in between. In certain embodiments, the method for repairing a degenerated disc in a patient in need thereof comprises injecting from 6.0 cc to about 8.0 cc. In certain embodiments, the method for repairing a degenerated disc in a patient in need thereof comprises injecting from 3.0 cc to about 6.0 cc. In some embodiments, the method for repairing a degenerated disc in a patient in need thereof comprises injecting about 0.1 cc to about 2.5 cc, including about 0.1 cc, about 0.5 cc, about 1.0 cc, about 1.5 cc, about 2.0 cc and about 2.5 cc, and all ranges there in between. In certain embodiments, the method for repairing a degenerated disc in a patient in need thereof comprises injecting from 0.5 to about 2.0 cc.

In some embodiments, the hydrogel of step (a) is heated to about 90° C. to about 130° C., including about 90° C., about 95° C., about 100° C., about 105° C., about 110° C., about 115° C., about 120° C., about 125° C., and about 130° C. including all ranges there between, to melt the hydrogel. In some embodiments, the hydrogel of step (a) is heated to about 90° C., about 95° C., about 100° C., about 105° C., about 110° C., about 115° C., about 120° C., about 125° C., or about 130° C. to melt the hydrogel. In some embodiments, the hydrogel of step (a) is heated to about 120° C. to melt the hydrogel.

In some embodiments, the hydrogel of step (a) is heated to about 120° C. to melt the hydrogel and the temperature is reduced to from about 60° C. to about 80° C. in step (b) to allow safe injection of the hydrogel into the patient. In certain embodiments, the hydrogel of step (a) is heated to about 120° C. to melt the hydrogel and the temperature is reduced to from about 65° C. to about 80° C. in step (b) to allow safe injection of the hydrogel into the patient.

In some embodiments, the present disclosure provides a method for replacing a nucleus pulposus in a patient in need thereof. In these embodiments, the nucleus pulposus is removed (or denucleated) to provide a cavity into which the compositions of the present disclosure are injected. The nucleus pulposus may be removed using methods that are known to those skilled in the art including the methods described in U.S. Pat. No. 8,475,532 and U.S. Patent Publication No. 2008/0027554, which are hereby incorporated by reference in their entirety for all purposes. In some embodiments, the method for replacing a nucleus pulposus in a patient in need thereof comprises (a) injecting an enzyme into the nucleus of intervertebral disc to dissolve the nucleus pulposus in need of replacement, (b) removing the dissolved tissue from nucleus of the intervertebral disc, and (c) injecting a therapeutically effective amount of a hydrogel of the present disclosure into the nucleus of intervertebral disc as described in FIG. 8A. A person of ordinary skill in the art (for example, an interventional radiologist or surgeon) could select an appropriate amount of an enzyme used in Step (a) as well as the amount of hydrogel used in Step (c). In some embodiments, the enzyme is a serine protease. In some embodiments, the enzyme is a Chondroitinase enzyme.

In some embodiments, the methods of the present disclosure provide a tissue implant having a Young's modulus of about 0.1 MPa to about 5 MPa, including about 0.5 MPa, about 1.0 MPa, about 1.5 MPa, about 2.0 MPa, about 2.5 MPa, about 3.0 MPa, about 3.5 MPa, about 4.0 MPa, and about 4.5 MPa, and all ranges there in between. In certain embodiments, the methods of the present disclosure provide a tissue implant having a Young's modulus of about 1.0 MPa to about 2.0 MPa. In certain embodiments, the methods of the present disclosure provide a tissue implant having a Young's modulus of about 0.1 MPa to about 1.0 MPa.

In some embodiments, the methods of the present disclosure provide a tissue implant having a Young's modulus of about 0.1 MPa, about 0.5 MPa, about 1.0 MPa, about 1.5 MPa, about 2.0 MPa, about 2.5 MPa, about 3.0 MPa, about 3.5 MPa, about 4.0 MPa, about 4.5 MPa or about 5.0 MPa. In certain embodiments, the methods of the present disclosure provide a tissue implant having a Young's modulus of about 0.1 MPa. In certain embodiments, the methods of the present disclosure provide a tissue implant having a Young's modulus of about 0.5 MPa.

In some embodiments, the needle in Step (c) has a needle gauge of about 15 gauge to about 22 gauge, including about 16 gauge, about 17 gauge, about 18 gauge, about 19 gauge, about 20 gauge, and about 21 gauge, and all ranges there in between. In certain embodiments, the needle gauge is about 17 gauge to about 19 gauge. In some embodiments, the needle in Step (c) has a needle gauge of about 15 gauge, about 16 gauge, about 17 gauge, about 18 gauge, about 19 gauge, about 20 gauge, about 21 gauge, or about 22 gauge. In certain embodiments, the needle in Step (c) has a needle gauge of about 17 gauge. In certain embodiments, the needle in Step (c) is a 152 mm Tuohy epidural needle.

In some embodiments, in Step (d), the needle is connected to the syringe via a flexible extension tube. In some embodiments, the flexible extension tube is constructed from a medical grade polymer, such as polyurethane. In some embodiments, the flexible extension tube is about 10 inches long. In some embodiments, the flexible extension tube is about 6 inches long. In certain embodiments, the flexible extension tube is about 160 mm long and has an inner diameter of about 1.59 mm.

In some embodiments, the injection rate of the hydrogel in Step (e) is greater than about 1.0 cc/min. In some embodiments, the injection rate of the hydrogel in Step (e) is greater than about 1.5 cc/min. In some embodiments, the injection rate of the hydrogel in Step (e) is greater than about 2.0 cc/min. In some embodiments, the injection rate of the hydrogel in Step (e) is greater than about 2.5 cc/min. In some embodiments, the injection rate of the hydrogel in Step (e) is greater than about 3.0 cc/min. In some embodiments, the injection rate of the hydrogel in Step (e) is greater than about 3.5 cc/min. In some embodiments, the injection rate of the hydrogel in Step (e) is greater than about 4.0 cc/min. In some embodiments, the injection rate of the hydrogel in Step (e) is greater than about 4.5 cc/min. In some embodiments, the injection rate of the hydrogel in Step (e) is greater than about 5.0 cc/min. In some embodiments, the injection rate of the hydrogel in Step (e) is greater than about 5.5 cc/min. In some embodiments, the injection rate of the hydrogel in Step (e) is greater than about 6.0 cc/min.

EXAMPLES

The present invention is further illustrated by reference to the following Examples. However, it is noted that these Examples, like the embodiments described above, are illustrative and are not to be construed as restricting the scope of the invention in any way.

Example 1: Preparation of Hydrogels of the Present Disclosure

Exemplary hydrogels of the present disclosure were prepared according to the following procedure. Raw materials were provided in the ratios shown in Table 1, below.

TABLE 1

| Raw Material Composition | | | |
|---|---|---|---|
| Material | Ex. 1A (wt. %) | Ex. 1B (wt. %) | Ex. 1C (wt. %) |
| Polyvinyl Alcohol (MW ~145,000 Da) | 12.4% | 12.4% | 22.3% |
| Polyvinylpyrrolidone (MW ~45,000 kDa) | 0.124% | 0.124% | 0.223% |
| Polyethylene Glycol | 17.50% | 17.50% | 22.5% |

TABLE 1-continued

Raw Material Composition

| Material | Ex. 1A (wt. %) | Ex. 1B (wt. %) | Ex. 1C (wt. %) |
|---|---|---|---|
| (MW ~1,000 kDa) | | | |
| Barium Sulfate | 8.3% | — | 6.5% |
| Silver Sulfate | — | 8.3% | — |
| Water | 61.70% | 61.70% | 48.5% |

The following raw materials were used: Polyvinyl alcohol (Polyvinyl alcohol 28-99 available from EMD Millipore), Polyvinylpyrrolidone (Povidone K-30 available from Spectrum Chemical), Polyethylene Glycol (Polyethylene Glycol 1000, NF available from Spectrum Chemical), Barium Sulfate (Barium Sulfate, U.S.P. available from J.T. Baker).

The PVA, PVP, and contrast agent solutions were prepared by mixing the PVA, PVP, and contrast agent in water using the masses recited in Table 2. The PVA, PVP, and contrast agent solutions were stirred for about two minutes. The resulting mixtures were heated to above the melting point (but not more than 200 degrees Celsius), and the solutions were held at this temperature for about 30 minutes. The temperature of the solutions was adjusted to about 85° C. and PEG was added to the solutions.

TABLE 2

Raw Material Mass

PVA, PVP and Contrast agent solution

| Example | PVA (g) | PVP (g) | BaSO$_4$ (g) | AgSO$_4$ (g) | water (g) | Total Mass (g) | PEG (g) |
|---|---|---|---|---|---|---|---|
| Ex. 1A | 13.98 | 0.14 | 9.34 | — | 69.77 | 93.23 | 19.77 |
| Ex. 1B | 13.98 | 0.14 | — | 9.34 | 69.77 | 93.23 | 19.77 |
| Ex. 1C | 25.20 | 0.25 | 7.35 | — | 54.81 | 87.60 | 24.42 |

The solutions were placed in a sealed container at about 22° C. for about three hours. After about three hours, the containers were opened, the supernatants decanted, and their weights recorded. The recorded weights were used to establish mass balance throughout the manufacturing process to the finished hydrogel. The polymer solutions were resealed in their respective containers and heated for about 30 minutes at 121° C.

Within 10 minutes after the end of the heating cycle, the containers were removed from the heat and supernatants were decanted, its weight is recorded, and discarded. The contents of the container were stirred for three minutes. The finished hydrogels were packaged in syringes.

Example 2: Injection of the Hydrogels of the Present Disclosure

The following example provides a representative injection procedure for augmenting (or replacing) a nucleus pulposus as well as certain injection properties of the hydrogels of the present disclosure.

Example 2a: Injection Procedure

Prior to use, the hydrogel-containing syringes prepared according to Example 1 may be heated for about 30 minutes at 121° C., and cooled to about 65° C. to reduce the hydrogel viscosity to about 10.7+/−1.3 Pascal seconds (Pa·s) prior to injection.

Referring to FIG. 2, for example, the hydrogel may injected into an intervertebral disc 50 using the assembly 200 described above. As described above, the injection apparatus 210 is connected to a length of flexible, high-pressure tubing 250 that is in turn connected to an injection needle 270. The arrangement allows the surgeon freedom of movement between the injection apparatus 210 and the needle 270.

The tubing 250 may be about 25 cm in length. With a syringe temperature of about 65° C., it is estimated that the hydrogel cools to about 50° C. due cooling during passage through the tubing 250 (25 cm in length) to the needle 270. This is a temperature high enough to allow flow (viscosity of about 25.1+/−6.4 Pa·s) but does not burn patient's tissue.

Prior to injecting the hydrogel into the disc, the disc can be de-nucleated by any of several known methods through the needle 270. For a nucleus having a volume of 1.8 cc, the volume can be filled with a hydrogel of the present disclosure in 46 seconds using an 18 gauge needle and in 42 seconds using a 17 gauge needle.

Using a similar procedure, the hydrogel may injected into an intervertebral disc 50 using the assembly 300.

Example 2b: Injection Properties

Experiments were conducted to determine the injection properties of the hydrogels of the present disclosure.

The hydrogel of Example 1A was placed in 3 mL syringes and injected through either a 17 gauge or 20 gauge 15.2 cm Tuohy epidural Needle connected to the syringe by a high pressure tube (length: 10-inch (or 25.4 cm); inner diameter: 0.071 inch (or 1.8034 mm)) while heated using a syringe heater at 65° C. Thus, the total path length between the heated syringe and the needle tip was about 40.6 cm.

Table 3 shows the pressure and force required to inject the Example 1A hydrogel through the 17 gauge needle. These data show that the Example 1A hydrogel may be injected at rates of 5.9 mL/min (or 5.9 cc/min) through a 17 gauge needle with a path length of 40.6 cm between the heated syringe and the needle.

TABLE 3

Injection Pressure and Force

| Rate (ml/min) | Raw Force (N) | | Pressure (kPa) | | Pressure (psi) | |
|---|---|---|---|---|---|---|
| | Avg. | St. Dev | Avg. | St. Dev | Avg. | St. Dev |
| 1 | 10.2 | 8.1 | 170 | 134 | 24.6 | 19.5 |
| 2 | 21.1 | 2.5 | 349 | 41 | 50.6 | 6.0 |
| 4 | 22.3 | 2.8 | 369 | 47 | 53.4 | 6.8 |
| 5.9 | 54.5 | 34.7 | 902 | 574 | 130.8 | 83.2 |

The test syringes failed when attempts were made to inject the hydrogel of Example 1A at through a 20 gauge needle.

Example 3: Compositional Change: Raw Materials→Hydrogels→Implants of the Present Disclosure The hydrogels and implants of the present disclosure do not require chemical crosslinking agents for gelation. Instead, the present hydrogels result from physical crosslinking due to interchain hydrogen bonding between the constituent polymers (e.g., PVA, PVP, and PEG) and intrachain hydrogen bonding due to polymer crystallization.

Persons of ordinary skill in the art will understand that because the present hydrogels are based on hydrogen bonding rather than chemical crosslinking (which is found in many other hydrogels), the composition of the input raw materials and the resulting hydrogels are not the same. Specifically, during manufacturing the raw materials are combined to provide the hydrogel and the aqueous supernatants from above the hydrogels are decanted (see, e.g., Example 1). The aqueous supernatants contain free polymers (i.e., not equilibrated into the hydrogel) in ratios that are not identical to the ratios found in the raw materials. Similarly, following injection, the composition of the implants of the present disclosure is different from the injected hydrogel compositions.

Table 4 shows the change in composition of Example 1A, from the input raw materials, the packaged hydrogel in the syringe and the concentrations by weight after allowing the composition to swell in a simulated spine disc environment (i.e., 0.2 MPa osmotic solution at 37 degrees Celsius) for one week:

TABLE 4

Compositional change for Example 1A

| Material | Raw Materials | Gel in Syringe | Gel in simulated spine disc for 7 days |
|---|---|---|---|
| Polyvinyl Alcohol (MW ~145,000 Da) | 12.4% | 17.0% | 13.9% |
| Polyvinylpyrrolidone (MW ~45,000 kDa) | 0.124% | 0.170% | 0.140% |
| Polyethylene Glycol (MW ~1,000 kDa) | 17.50% | 13.8% | 13.8% |
| Barium Sulfate | 8.3% | 16.8% | 6.2% |
| Water | 61.70% | 52.5% | 64.1% |

Example 4: In Vivo Model Using the Hydrogels of the Present Disclosure

The following example established proof of concept regarding the use of the hydrogels of the present disclosure to treat degenerative disc disease in a large mammal. The purpose of the study was to demonstrate test article delivery (i.e., delivery of the hydrogels of the present disclosure), postoperative survival, and in vivo performance of the hydrogels of the present disclosure using in situ chemonucleolysis followed by nucleoplasty in a goat model that recapitulates intervertebral disc degeneration. Chemonucleolysis was conducted using Chondroitinase ABC protease free (lyophilized) ("CABC").

Test Article: A hydrogel having the composition of Example 1a (Tables 1-3, above) was supplied.

Figure 9:
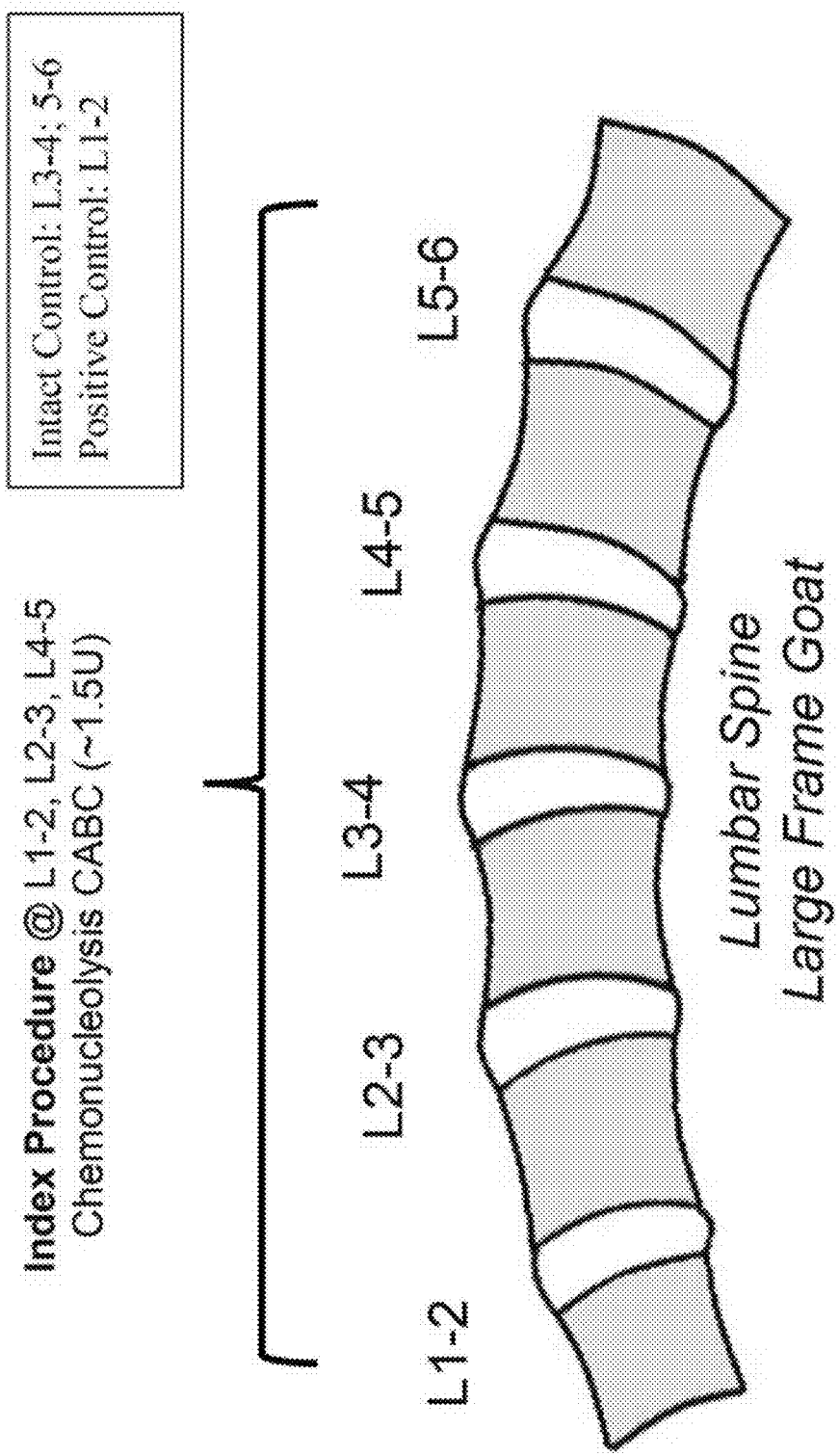
FIG. 9 shows the lumbar spine of a large frame goat and illustrates the study design used in Example 4.

Protocol Summary: A goat lumbar spine showing the study design is illustrated in FIG. 9. CABC was injected in three levels of the lumbar spine (L1-2, L2-3 and L4-5) to induce chemonucleolysis and following an induction period, the test article was administered by surgical implantation into two of the CABC-treated lumbar levels (L2-3 and L4-5). One CABC-treated lumbar level (L1-2) was a positive control. L3-4 and 5-6 were negative controls.

Delivery of Test Article: About 7-14 days following chemonucleolysis, goats were re-anesthetized and an open, left retroperitoneal transpsoatic approach was used to access the lumbar spine. Fluoroscopy was used to identify the treatment levels. The intervertebral disc of the respective lumbar levels was palpated and a 19 gauge spinal needle was advanced into the center of the nucleus pulposus.

Test Article delivery was performed under fluoroscopic guidance. Volume delivered was recorded. The test article was the hydrogel from Example 1A.

Postoperative Procedures: The goats recovered from anesthesia under close observation by a veterinarian and his/her designee. After recovery, goats were moved to a dedicated stall and released to a barn for the remainder of the study.

Clinical Observations: Days 1-3 postoperative: The animals were assessed for postoperative pain and from day 3 to 7 they were assessed once a day in the morning. All observations were recorded in individual medical record charts by veterinarians.

Imaging:

Digital Radiography: Standard ventro-dorsal digital radiographs of the lumbar spine were obtained in all animals preoperatively and were used to monitor the status of the indwelling implants postoperative.

Radiographic Exams: These exams were done at least preoperatively for screening purposes, within a few days postoperative and at midterm and end term respectively.

Intra-operative fluoroscopy was performed for surgical guidance.

Post-operative MRI: At least postoperative in vivo and/or end term MRI

CT: Computed Tomography may be performed preoperative prior to nucleoplasty. Images will be reconstructed in 3D.

Figure 10:
FIG. 10 shows a radiograph of the lumbar spine of a living goat from the Example 4 after chemonucleolysis using Chondroitinase ABC protease ("C-ABC") and prior to injection of a hydrogel of the present disclosure.

End of study: The animals were sacrificed at various periods and the following postmortem observations will be made:
(1) Gross necropsy
(2) Macroscopic evaluation
(3) MicroCT
(4) Histopathology:
(5) Test Article Analysis FIG. 10 shows a radiograph of the lumbar spine of a living goat after chemonucleolysis using CABC and prior to injection of the hydrogel of the present disclosure.

Figure 11:
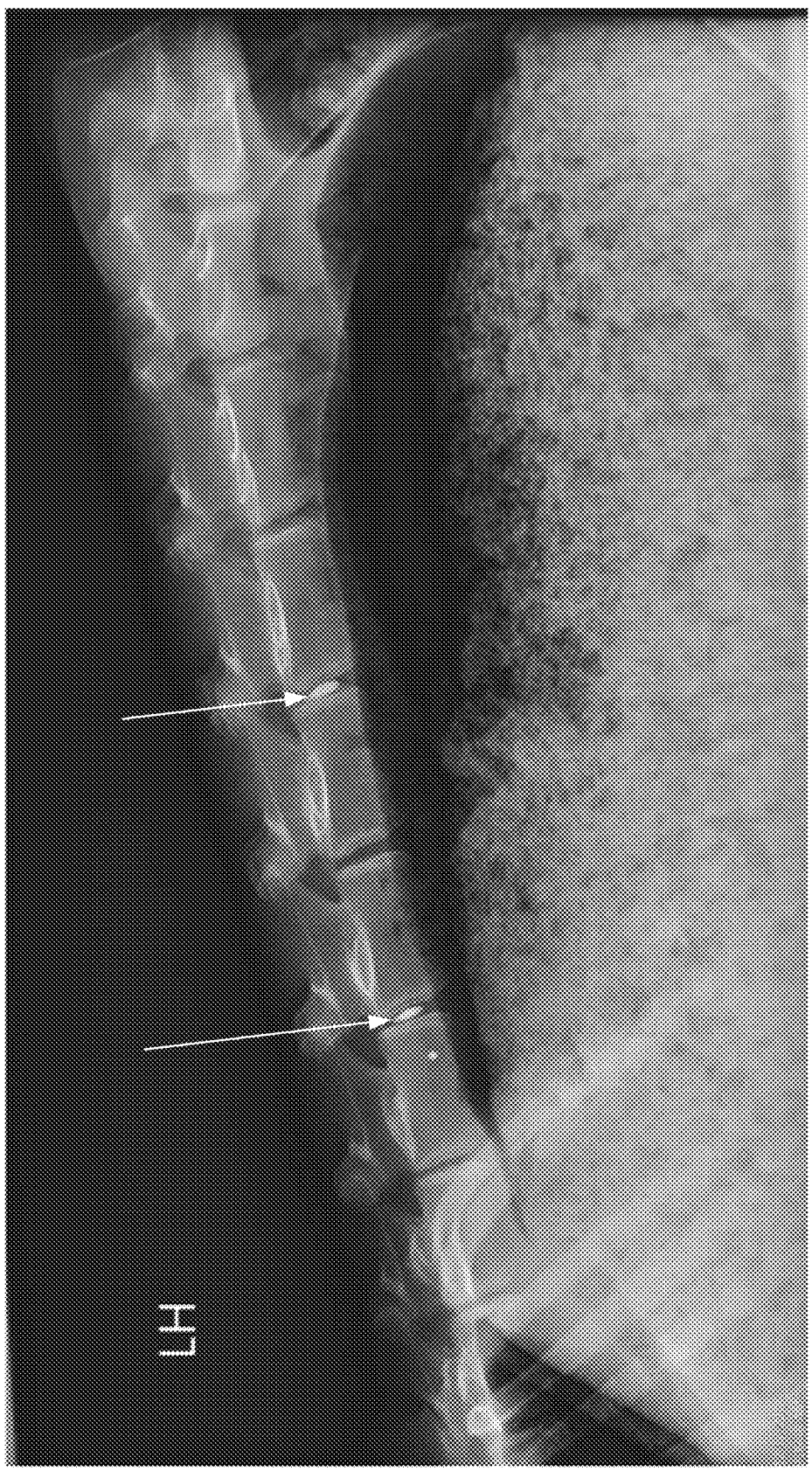
FIG. 11 shows a radiograph indicating the location of two nucleus implants implanted into the intervertebral disc within the lumbar spine of a living goat from the Example 4. The radiograph was taken four days after injection of a hydrogel of the present disclosure. The arrows indicate the location of the implants.

FIG. 11 shows a radiograph indicating the location of two nucleus implants in the lumbar spine of a living goat treated according to the protocol described above. The radiograph was taken four days after injection of a hydrogel of the present disclosure. The arrows indicate the location of the implants. The lateral radiograph indicates that the nucleus implants are well positioned, intact, and stable, and exhibit a coherent form 4 days after injection of the hydrogel of the present disclosure.

Figure 12:
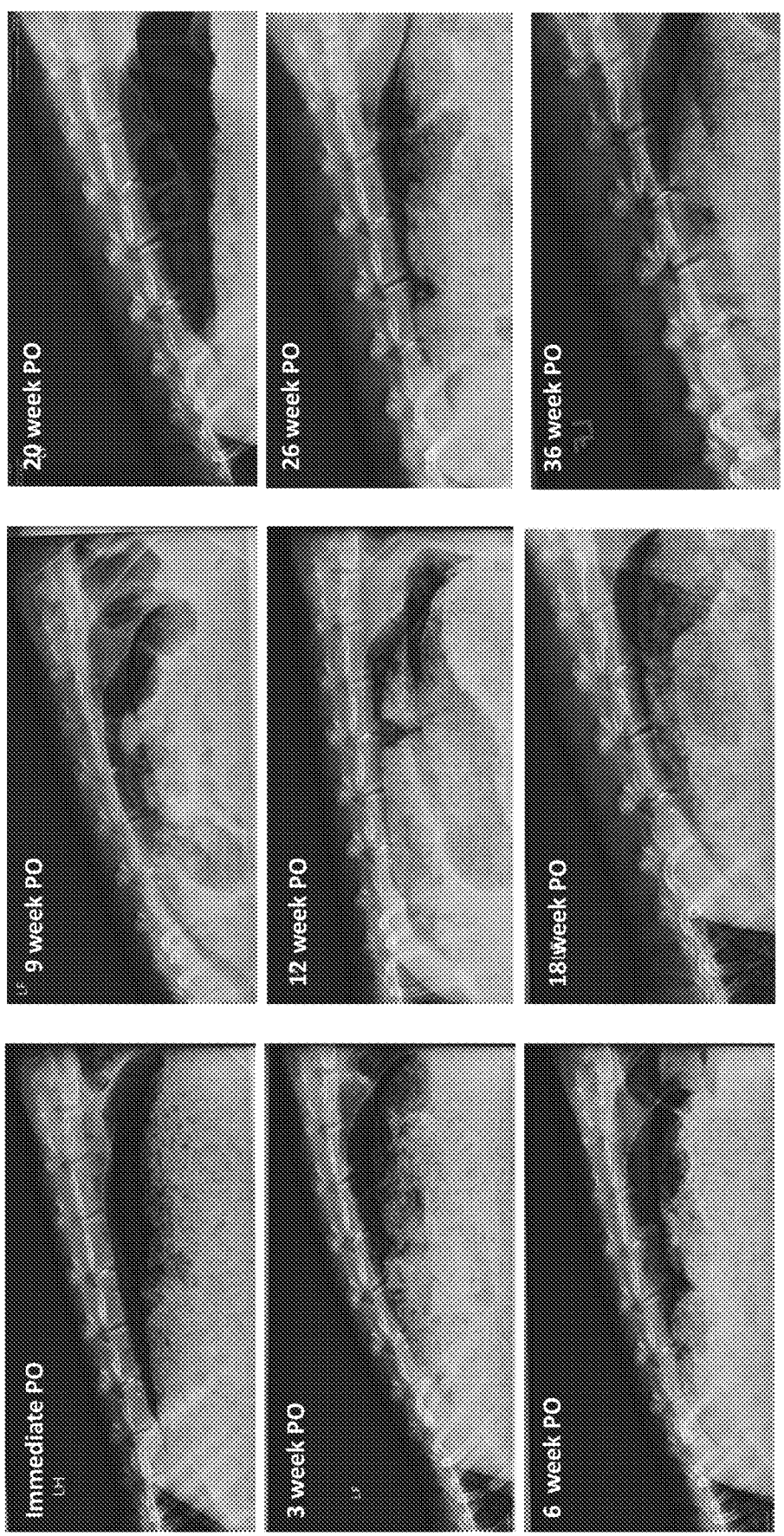
FIG. 12 shows a series of radiographs from the same goat indicating the location of two nucleus implants within the lumbar spine of a living goat from the Example 4. The radiographs were taken between implantation and 9 months.

FIG. 12 shows a series of radiographs from the same animal between implantation and 9 months indicating the location of two nucleus implants in the lumbar spine of a living goat treated according to the protocol described above. Notably, the implants did not migrate, expulse or show any radiographic signs of endplate damage in the animal during the course of evaluation. The animal survived more than one year without any adverse effects or implant expulsion or migration and the implants maintained the disc height in the treated segments while the positive control experienced a reduction in disc height (data not shown).

Example 5: Biomechanical Study of the Hydrogels of the Present Disclosure in a Degenerated Goat Spine The following study was conducted to study nucleus implant biomechanics on a degenerated cadaver goat model that are not possible in living patients.

Disc Model Preparation: Cadaver goat spines were cleaned of excess tissue, and lumbar vertebrae cut in half to isolate discs and adjacent endplates. The discs were treated using Chondroitinase ABC protease free (lyophilized) ("CABC") to provide a degenerated state. The endplates were secured to a mechanical testing unit in preparation for biomechanics testing.

Biomechanics Testing: Cyclic loading studies was performed to simulate cyclic patterns of a spine disc in use. This is performed both before and after the test article injection (i.e., the hydrogel) to determine biomechanics of the disc before restoration (CABC degenerated state) and after restoration (Gel injection). The disc was compressed to 80 N and relaxed to 15 N at a rate of 50 N/sec for 5 cycles. At the end of 5 cycles, the disc was compressed to 15 N, and held at that extension until the operator stops the experiment.

Test Article: A hydrogel of the present disclosure having the composition of Example 1a (Tables 1-3, above) was supplied.

Test Article Injection: A 160 cm, 17 gauge catheter was inserted to the mid-point of the disc under fluoroscopic guidance. Volume delivered was recorded by the start and end points of the syringe plunger. Pressure was monitored using the pressure gauge on the delivery device. Force on the disc was measured continuously by the mechanical testing unit.

Figure 13:
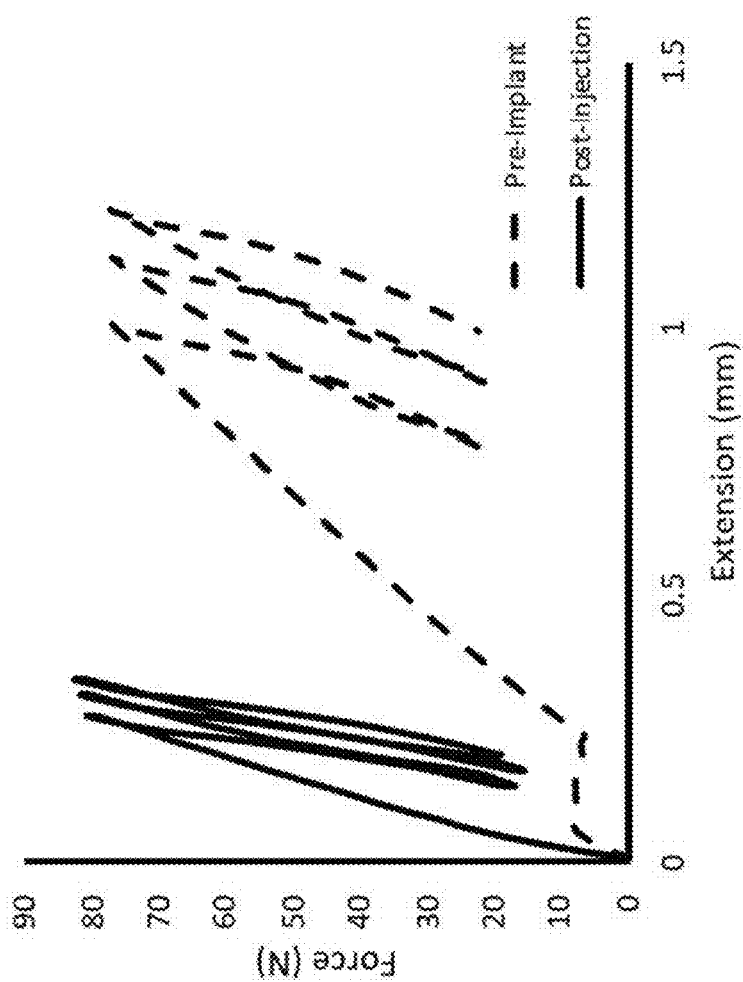
FIG. 13 shows the results of a biomechanical study of the present hydrogel in a degenerated goat spine from the Example 5.

FIG. 13 shows the results of a biomechanical study of the present hydrogel in a degenerated goat spine. Prior to hydrogel implantation the extension required on the tensile tester to reach a pre-specified force of 80 N started at about 0.75 mm and increased to 1 mm with repeated cycles, indicating fatigue of the degenerated disc. After implantation of an embodiment of the hydrogel described herein the extension required decreases dramatically, requiring only about 0.25 mm to reach the pre-specified 80 N mark, and remains relatively constant under repeated cycling.

It will be further understood that various changes in the details, materials, and arrangements of the parts which have been described and illustrated in order to explain the nature of this invention may be made by those skilled in the art without departing from the scope of the invention as expressed in the following claims.

While various embodiments have been described above, it should be understood that they have been presented by way of example only, and not limitation. Where schematics and/or embodiments described above indicate certain components arranged in certain orientations or positions, the arrangement of components may be modified. While the embodiments have been particularly shown and described, it will be understood that various changes in form and details may be made. Although various embodiments have been described as having particular features and/or combinations of components, other embodiments are possible having a combination of any features and/or components from any of embodiments described herein, except mutually exclusive combinations. The embodiments described herein can include various combinations and/or sub-combinations of the functions, components, and/or features of the different embodiments described.

The specific configurations of the various components can also be varied. For example, the size and specific shape of the various components can be different from the embodiments shown, while still providing the functions as described herein. More specifically, the size and shape of the various components can be specifically selected for a desired or intended usage. Thus, it should be understood that the size, shape, and/or arrangement of the embodiments and/or components thereof can be adapted for a given use unless the context explicitly states otherwise.

Where methods and/or events described above indicate certain events and/or procedures occurring in certain order, the ordering of certain events and/or procedures may be modified. Additionally, certain events and/or procedures may be performed concurrently in a parallel process when possible, as well as performed sequentially as described above.

EMBODIMENTS

1. A hydrogel, comprising:
   at least one polymer; and
   a solvent,
   wherein at a temperature of about 65° C. the hydrogel is capable of injection through a 16 cm length, 17 gauge needle at an injection rate of at least 1.0 cc per minute using an injection pressure of about 50 psi to provide a tissue implant having a Young's modulus of between about 0.1 to 5.0 MPa.
2. The hydrogel of embodiment 1, wherein the at least one polymer is selected from the group consisting of polyvinyl alcohol, polyvinylpyrrolidone and polyethylene glycol.
3. The hydrogel of any one of embodiments 1-2, wherein the hydrogel comprises polyvinyl alcohol, polyvinylpyrrolidone and polyethylene glycol.
4. The hydrogel of any one of embodiments 2-3, wherein the polyvinyl alcohol has an Mw of between about 60,000 Da to about 190,000 Da.
5. The hydrogel of any one of embodiments 2-4, wherein the polyethylene glycol has an Mw of about 100 Da to about 4600 Da.
6. The hydrogel of any one of embodiments 2-5, wherein the polyvinylpyrrolidone has an Mw of about 5,000 Da to about 60,000 Da.
7. The hydrogel of any one of embodiments 1-6, wherein the solvent is selected from the group consisting of water, dimethylsulfoxide, saline, or a phosphate buffer.
8. The hydrogel of any one of embodiments 1-7, further comprising a contrast agent.
9. The hydrogel of embodiment 8, wherein the contrast agent is barium sulfate.
10. The hydrogel of any one of embodiments 1-9, further comprising a dye or colorant.
11. The hydrogel of any one of embodiments 1-10, wherein the hydrogel is capable of injection at an injection rate of at least 2.5 cc per minute.
12. The hydrogel of any one of embodiments 1-11, wherein the hydrogel is capable of injection at an injection rate of at least 3.0 cc per minute.
13. The hydrogel of any one of embodiments 1-12, wherein the tissue is selected from the group consisting of nucleus of an intervertebral disc and the submucosal space under the ureteric orifice.
14. The hydrogel of embodiment 13, wherein the tissue is the nucleus of an intervertebral disc.
15. The hydrogel of any one of embodiments 1-14, wherein the hydrogel has a viscosity of about 10 Pa·s at a temperature of about 65° C.
16. The hydrogel of any one of embodiments 1-15, wherein the hydrogel is packaged in a syringe.
17. A hydrogel, comprising:
   about 12 wt. % to about 22 wt. % of polyvinyl alcohol;
   about 0.12 wt. % to about 0.22 wt. % of polyvinylpyrrolidone and;

about 12 wt. % and about 22 wt. % polyethylene glycol; and a solvent.

18. The hydrogel of embodiment 17, wherein at a temperature of about 65° C. the hydrogel is capable of injection through a 16 cm length, 17 gauge needle at an injection rate of at least 2.0 cc per minute using an injection pressure of about 50 psi to provide a tissue implant having a Young's modulus of between about 0.1 to 5.0 MPa.

19. The hydrogel of any one of embodiments 17-18, wherein the hydrogel is capable of injection at an injection rate of at least 2.5 cc per minute.

20. The hydrogel of any one of embodiments 17-19, wherein the hydrogel is capable of injection at an injection rate of at least 3.0 cc per minute.

21. The hydrogel of any one of embodiments 17-20, wherein the hydrogel comprises:
about 17 wt. % of polyvinyl alcohol;
about 0.17 wt. percent of polyvinylpyrrolidone; and
about 16.8 wt. % of polyethylene glycol.

22. The hydrogel of any one of embodiments 17-21, wherein
the polyvinyl alcohol has an Mw of about 60,000 Da to about 190,000 Da;
the polyethylene glycol has an Mw of about 100 Da to about 4600 Da; and
the polyvinylpyrrolidone has an Mw of about 5,000 Da to about 60,000 Da.

23. The hydrogel of any one of embodiments 17-22, wherein the solvent is selected from the group consisting of water, dimethyl sulfoxide, saline, or a phosphate buffer.

24. The hydrogel of any one of embodiments 17-23, further comprising a contrast agent.

25. The hydrogel of embodiment 24, wherein the contrast agent is barium sulfate.

26. The hydrogel of any one of embodiments 17-25, further comprising a visualization agent.

27. The hydrogel of any one of embodiments 17-26, wherein the tissue is selected from the group consisting of the nucleus of an intervertebral disc and the submucosal space under the ureteric orifice.

28. The hydrogel of embodiment 27, wherein the tissue is the nucleus of an intervertebral disc.

29. The hydrogel of any one of embodiments 17-28, wherein the hydrogel has a viscosity of about 10 Pa·s at a temperature of about 65° C.

30. The hydrogel of any one of embodiments 17-29, wherein the hydrogel is packaged in a syringe.

30a. The hydrogel of any one of embodiments 1-30, wherein the hydrogel does not contain a chemically cross-linked polymer.

30b. The hydrogel of any one of embodiments 1-30a, wherein the polyethylene glycol has an Mw of about 100 Da to about 4600 Da.

30c. The hydrogel of any one of embodiments 1-30b, wherein the polyethylene glycol has an Mw of about 800 Da to about 2000 Da.

30d. The hydrogel of any one of embodiments 1-30c, wherein the polyethylene glycol has an Mw of about 1000 Da.

30e. The hydrogel of any one of embodiments 1-30d, wherein the solvent is water.

30f. The hydrogel of any one of embodiments 1-30e, wherein the hydrogel is not a theta-gel.

30g. The hydrogel of any one of embodiments 1-30f, wherein the wt. % of the aqueous supernatant changes less than about 5 wt. % when the hydrogel is stored at 23° C. for 2 months.

30h. The hydrogel of any one of embodiments 1-30e, wherein the polyethylene glycol is non-functionalized PEG.

31. A tissue implant having a Young's modulus of between about 0.1 to 5.0 MPa, wherein the tissue implant is formed by the injection of a hydrogel into a living patient's tissue,
wherein the hydrogel comprises:
at least one polymer; and
a solvent,
wherein at a temperature of about 65° C. the hydrogel is capable of injection through a 16 cm length, 17 gauge needle at an injection rate of at least 2.0 cc per minute using an injection pressure of about 50 psi.

32. The tissue implant of embodiment 31, wherein the tissue is the nucleus of an intervertebral disc.

33. A tissue implant having a Young's modulus of between about 0.1 to 5.0 MPa, wherein the tissue implant is formed by the injection of a hydrogel into a living patient's tissue,
wherein the hydrogel comprises:
about 12 wt. % to about 22 wt. % of polyvinyl alcohol;
about 0.12 wt. percent to about 0.22 wt. % of polyvinylpyrrolidone;
about 12 wt. % and about 22 wt. % polyethylene glycol; and
a solvent.

34. The tissue implant of embodiment 33, wherein at a temperature of about 65° C. the hydrogel is capable of injection through a 16 cm length, 17 gauge needle at an injection rate of at least 2.0 cc per minute using an injection pressure of about 50 psi.

35. The tissue implant of embodiment 34, wherein the tissue is the nucleus of an intervertebral disc.

36. A method of repairing or supplementing a tissue in a patient in need thereof, comprising:
(a) melting a hydrogel of the present disclosure in a container;
(b) heating the mixture of step (a) to from about 65° C. to about 80° C.;
(c) inserting a 15 gauge or smaller needle into the tissue in need of repair or supplement;
(d) connecting the needle to the container and
(e) injecting a therapeutically effective amount of the step (b) mixture into the tissue to provide a tissue implant,
wherein at a temperature of about 65° C. the hydrogel is capable of injection through a 16 cm length, 17 gauge needle at an injection rate of at least 2.0 cc per minute using an injection pressure of about 50 psi to provide a tissue implant having a Young's modulus of between about 0.1 to 5.0 MPa.

37. The method of embodiment 36, wherein the tissue is the nucleus of an intervertebral disc.

38. The method of any one of embodiments 36-37, wherein the needle is a 17 gauge needle.

39. The method of any one of embodiments 36-37, wherein the needle is an 18 gauge needle.

40. The method of any one of embodiments 36-39, wherein the injection rate of the hydrogel into the tissue is at least 2.5 cc per minute.

41. The method of any one of embodiments 36-40, wherein the injection rate of the hydrogel into the tissue is at least 3.0 cc per minute.
42. The method of any one of embodiments 36-41, wherein the therapeutically effective amount of the step (b) mixture is about 1.8 cc.
43. A method of repairing or supplementing a tissue in a patient in need thereof, comprising:
    (a) melting a hydrogel in a container, wherein the hydrogel comprises:
        about 12 wt. % to about 22 wt. % of polyvinyl alcohol;
        about 0.12 wt. percent to about 0.22 wt. % of polyvinylpyrrolidone;
        about 12 wt. % and about 22 wt. % polyethylene glycol; and
        a solvent;
    (b) heating the step (a) mixture to from about 65° C. to about 80° C.;
    (c) inserting a 15 gauge or smaller needle into the tissue in need of repair or supplement;
    (d) connecting the needle to the container and
    (e) injecting a therapeutically effective amount of the step (b) mixture into the tissue to provide a tissue implant.
44. The method of embodiment 43, wherein at a temperature of about 65° C. the hydrogel is capable of injection through a 16 cm length, 17 gauge needle at an injection rate of at least 2.0 cc per minute using an injection pressure of about 50 psi to provide a tissue implant having a Young's modulus of between about 0.1 to 5.0 MPa.
45. The method of any one of embodiments 43-44, wherein the tissue is the nucleus of an intervertebral disc.
46. The method of any one of embodiments 43-45, wherein the needle is a 17 gauge needle.
47. The method of any one of embodiments 43-46, wherein the needle is an 18 gauge needle.
48. The method of any one of embodiments 43-47, wherein the injection rate of the hydrogel into the tissue is at least 2.5 cc per minute.
49. The method of any one of embodiments 43-48, wherein the injection rate of the hydrogel into the tissue is at least 3.0 cc per minute.
50. The method of any one of embodiments 43-49, wherein the tissue implant has a Young's modulus of between about 0.1 to 1.0 MPa.
51. The method of any one of embodiments 43-50, wherein the therapeutically effective amount of the step (b) mixture is about 1.8 cc.
52. The method of any one of embodiments 36-51, further comprising:
    inserting the syringe into an injector after filling the syringe with the hydrogel.
53. The method of embodiment 52, wherein the injector includes a heater assembly, the melting of step (a) and the heating of step (b) including melting and heating the hydrogel via the heater assembly.
54. The method of embodiment 52, wherein the injector includes an actuator, the injecting of step (e) including transitioning the actuator from a first state to a second state.
55. The method of embodiment 54, wherein transitioning the actuator from the first state to the second state includes moving a plunger from a proximal position within the syringe to a distal position within the syringe.
56. The method of embodiment 54 or 55, wherein the actuator is configured to transition from the first state to the second state in response to being rotated relative to the syringe.
57. The method of any one of embodiments 36-56, wherein the hydrogel of step (a) is heated to about 121° C. to melt the hydrogel.
58. The method of any of embodiments 36-57, wherein the therapeutically effective amount of the step (b) mixture is from about 0.1 cc to about 12.0 cc.
59. The method of any of embodiments 36-57, wherein the therapeutically effective amount of the step (b) mixture is from about 3.0 cc to about 6.0 cc.
60. The method of any of embodiments 36-57, wherein the therapeutically effective amount of the step (b) mixture is from about 6.0 cc to about 8.0 cc.
61. The method of any of embodiments 36-60, wherein the hydrogel does not contain a chemically cross-linked polymer.
62. The method of any of embodiments 36-61, wherein the polyethylene glycol has an Mw of about 100 Da to about 4600 Da.
63. The method of any of embodiments 36-62, wherein the polyethylene glycol has an Mw of about 800 Da to about 2000 Da.
64. The method of any of embodiments 36-62, wherein the polyethylene glycol has an Mw of about 1000 Da.
65. The method of any of embodiments 36-62, wherein the solvent is water.
66. A method of manufacturing a hydrogel comprising:
    (a) forming a mixture of at least one polymer and a solvent;
    (b) stirring the mixture of step (a);
    (c) melting the stirred mixture of step (b) to form a solution; and
    (d) cooling the solution of step (c) to provide a hydrogel,
    wherein at a temperature of about 65° C. the hydrogel is capable of injection through a 16 cm length, 17 gauge needle at an injection rate of at least 2.0 cc per minute using an injection pressure of about 50 psi to provide a tissue implant having a Young's modulus of between about 0.1 to 5.0 MPa.
67. A method of manufacturing a hydrogel comprising:
    about 12 wt. % to about 22 wt. % of polyvinyl alcohol;
    about 0.12 wt. percent to about 0.22 wt. % of polyvinylpyrrolidone;
    about 12 wt. % and about 22 wt. % polyethylene glycol; and
    a solvent, the method comprising:
    (a) forming a mixture of polyvinyl alcohol, polyvinylpyrrolidone, polyethylene glycol and a solvent;
    (b) stirring the mixture of step (a);
    (c) melting the stirred mixture of step (b) to form a solution; and
    (d) cooling the solution of step (c).
68. A method of manufacturing a hydrogel comprising:
    (a) forming a mixture comprising PVA, PVP and water;
    (b) heating the mixture of Step (a) to form a solution;
    (c) heating polyethylene glycol having a Mw of about 800 Da to about 2,000 Da;
    (d) adding the heated PEG from step (c) to the heated mixture of step (b);

(e) cooling the mixture of step (d) to provide a hydrogel;
(f) conducting a phase separation to provide an aqueous supernatant and a hydrogel; and
(g) removing the aqueous supernatant to provide the hydrogel.

69. The method of embodiment 68, wherein the heating of step (b) is from about 95° C. to about 120° C.

70. The method of any one of embodiments 68-69, wherein the heating of step (c) is from about 95° C. to about 120° C.

71. The method of any one of embodiments 68-69, wherein the phase separation is conducted by centrifugation.

72. The method embodiment 71, wherein the centrifugation is conducted at from about 4,000 g to about 6,000 g for from about 5 min to about 10 min.

73. The method embodiment 71, wherein the centrifugation is conducted at about 4,300 g for about 10 min.

74. The method of any one of embodiments 71-73, wherein the centrifugation is conducted at a speed and for a time that is sufficient to achieve phase separation but does not form a density gradient of suspended contrast agent.

75. The method of any one of embodiments 68-74, wherein the mixture of step (a) further comprises a contrast agent.

76. The method of embodiment 75, wherein the contrast agent is barium sulfate.

77. The method of any one of embodiments 68-74, wherein the mixture of step (e) comprises:
about 7 wt. % to about 17 wt. % of polyvinyl alcohol;
about 0.07 wt. % to about 0.17% of polyvinylpyrrolidone;
about 13 wt. % to about 23 wt. % of polyethylene glycol;
about 3 wt. % to about 13 wt. % of barium sulfate and about 57 wt. % to about 67 wt. % of water.

78. The method of any one of embodiments 68-74, wherein the mixture of step (e) comprises:
about 9 wt. % to about 15 wt. % of polyvinyl alcohol;
about 0.09 wt. % to about 0.15% of polyvinylpyrrolidone;
about 15 wt. % to about 21 wt. % of polyethylene glycol;
about 5 wt. % to about 11 wt. % of barium sulfate and about 59 wt. % to about 65 wt. % of water.

79. The method of any one of embodiments 68-74, wherein the mixture of step (e) comprises:
about 11 wt. % to about 13 wt. % of polyvinyl alcohol;
about 0.11 wt. % to about 0.13% of polyvinylpyrrolidone;
about 17 wt. % to about 19 wt. % of polyethylene glycol;
about 7 wt. % to about 9 wt. % of barium sulfate and about 61 wt. % to about 63 wt. % of water.

80. The method of any one of embodiments 68-79, wherein the hydrogel does not contain a chemically cross-linked polymer.

81. The method of any one of embodiments 68-80, wherein the polyethylene glycol has an Mw of about 800 Da to about 2000 Da.

82. The method of any one of embodiments 68-81, wherein the polyethylene glycol has an Mw of about 1000 Da.

83. The method of any one of embodiments 68-82, wherein the hydrogel is not a theta-gel.

84. The method of any one of embodiments 68-83, wherein the wt. % of the aqueous supernatant changes less than about 5 wt. % when the hydrogel is stored at 23° C. for 2 months.

85. The method of any one of embodiments 68-84, wherein the polyethylene glycol is non-functionalized PEG.

86. The method of any one of embodiments 68-85, wherein the hydrogel comprises:
about 12 wt. % to about 22 wt. % of polyvinyl alcohol;
about 0.12 wt. percent to about 0.22 wt. % of polyvinylpyrrolidone;
about 12 wt. % to about 22 wt. % non-functionalized polyethylene glycol having
a Mw of about 800 Da to about 2,000 Da, wherein the hydrogel does not contain a chemically crosslinked polymer.

87. The hydrogel prepared by the method of any one of embodiments 68-87.

The invention claimed is:

1. A method of repairing or supplementing a tissue in a patient in need thereof, comprising:
(a) melting a hydrogel in a container, wherein the hydrogel comprises:
about 12 wt. % to about 22 wt. % of polyvinyl alcohol;
about 0.12 wt. % to about 0.22 wt. % of polyvinylpyrrolidone; and
about 12 wt. % to about 22 wt. % of non-functionalized polyethylene glycol having a Mw of about 800 Da to about 2,000 Da, wherein the hydrogel does not contain a chemically crosslinked polymer; and
a solvent;
and
(b) injecting a therapeutically effective amount of the melted hydrogel, wherein the hydrogel does not contain a chemically cross-linked polymer, through a 15 gauge or smaller needle into the tissue in need of repair or supplement to provide a tissue implant.

2. The method of claim 1, wherein the tissue is the nucleus of an intervertebral disc.

3. The method of claim 2, further comprising injecting an enzyme into the nucleus of the intervertebral disc to dissolve the nucleus pulposus before injecting the melted hydrogel.

4. The method of claim 2, wherein the method further comprises determining the therapeutically effective amount of the melted hydrogel by observing the implant in real time as it the melted hydrogel is injected using radiographic imaging.

5. The method of claim 2, wherein the method further comprises determining the therapeutically effective amount of the melted hydrogel by:
(a) injecting the melted hydrogel to achieve a pressure of about 120 psi to about 200 psi as determined by a pressure gauge on a delivery system;
(b) pausing the melted hydrogel injection;
(c) monitoring the pressure gauge for a pressure decrease below 120 psi to about 200 psi;
(d) injecting additional melted hydrogel until 120 psi to about 200 psi is achieved; and
(e) repeating the steps (b)-(d) until the pressure decrease is less than about 10% of 120 psi to about 200 psi.

6. A kit for disc augmentation, comprising:
about 1 cc to about 6 cc of a hydrogel packaged in a suitable container,
wherein the hydrogel comprises:
about 12 wt. % to about 22 wt. % of polyvinyl alcohol;

about 0.12 wt. % to about 0.22 wt. % of polyvinylpyrrolidone;

about 12 wt. % to about 22 wt. % of non-functionalized polyethylene glycol having a Mw of about 800 Da to about 2,000 Da, wherein the injectable form of the hydrogel does not contain a chemically crosslinked polymer and the injectable form of the hydrogel is injectable at about 65° C. through a 15-gauge needle into the nucleus of a human patient's intervertebral disc.

7. The kit of claim 6, wherein the non-functionalized polyethylene glycol has an Mw of about 800 Da to about 1,200 Da.

8. The kit of claim 6, wherein the hydrogel further comprises a contrast agent.

9. The kit of claim 8, wherein the contrast agent is barium sulfate.

10. The kit of claim 8, wherein the hydrogel comprises about 9 wt. % to about 19 wt. % of the contrast agent.

11. The kit of claim 6, wherein the polyvinyl alcohol has a Mw of about 135,000 Da to about 155,000 Da.

12. The kit of claim 6, wherein the polyvinylpyrrolidone has a Mw of about 35,000 Da to about 55,000 Da.

13. The kit of claim 6, further comprising a hydrogel delivery system, wherein the hydrogel delivery system comprises a syringe assembly.

14. The kit of claim 13, wherein the syringe assembly comprises a heater assembly.

15. The kit of claim 6, wherein the suitable container is a syringe.

* * * * *